(12) United States Patent
Vu et al.

(10) Patent No.: US 7,638,512 B2
(45) Date of Patent: Dec. 29, 2009

(54) PHENYLAMINOPROPANOL DERIVATIVES AND METHODS OF THEIR USE

(75) Inventors: An Thien Vu, Pottstown, PA (US); Paige Erin Mahaney, Pottstown, PA (US); Stephen Todd Cohn, Reading, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 12/144,363

(22) Filed: Jun. 23, 2008

(65) Prior Publication Data

US 2008/0255102 A1 Oct. 16, 2008

Related U.S. Application Data

(62) Division of application No. 11/091,291, filed on Mar. 28, 2005, now Pat. No. 7,414,052.

(60) Provisional application No. 60/557,831, filed on Mar. 30, 2004, provisional application No. 60/569,861, filed on May 11, 2004.

(51) Int. Cl.
- A61K 31/54 (2006.01)
- C07D 279/10 (2006.01)
- C07D 279/12 (2006.01)
- C07D 295/00 (2006.01)

(52) U.S. Cl. .................. 514/224.2; 544/56; 544/59

(58) Field of Classification Search ............... 514/224.2; 544/56, 59
See application file for complete search history.

(56) References Cited

U.S. PATENT DOCUMENTS

| | | | |
|---|---|---|---|
| 3,454,554 A | 7/1969 | Biel et al. | 260/239 |
| 4,123,543 A | 10/1978 | Jonsson et al. | 424/272 |
| 4,221,919 A | 9/1980 | Grimova et al. | 562/465 |
| 4,229,449 A | 10/1980 | Melloni et al. | 514/239.2 |
| 4,271,160 A | 6/1981 | Melloni et al. | 514/233.8 |
| 4,310,524 A | 1/1982 | Wiech et al. | 514/217 |
| 4,535,186 A | 8/1985 | Husbands et al. | 564/336 |
| 4,826,844 A | 5/1989 | Husbands et al. | 514/252 |
| 5,502,047 A | 3/1996 | Kavey | 514/183 |
| 5,516,774 A | 5/1996 | Albright et al. | 514/220 |
| 5,648,511 A | 7/1997 | Ng et al. | 558/345 |
| 6,380,155 B1 | 4/2002 | Barazanji et al. | 514/2 |
| 6,703,389 B2 | 3/2004 | Wong et al. | 514/239.2 |
| 2002/0107249 A1 | 8/2002 | Wong et al. | 514/238.5 |
| 2003/0008860 A1 | 1/2003 | Bakker-Arkema et al. | 514/215 |
| 2003/0069236 A1* | 4/2003 | Vianello et al. | 514/230.5 |
| 2004/0019101 A1 | 1/2004 | Karlstadt et al. | 514/464 |
| 2004/0143008 A1 | 7/2004 | Deecher et al. | 514/521 |
| 2004/0152710 A1 | 8/2004 | Deecher et al. | 514/255.04 |
| 2004/0180879 A1 | 9/2004 | Deecher et al. | 514/225.8 |
| 2005/0130987 A1 | 6/2005 | Deecher et al. | 514/253.05 |
| 2005/0143394 A1 | 6/2005 | Mahaney et al. | 514/255.04 |
| 2005/0148579 A1 | 6/2005 | Trybulski et al. | 544/398 |
| 2005/0148595 A1 | 7/2005 | Mahaney | 514/252.12 |
| 2005/0165082 A1 | 7/2005 | Leventhal et al. | 514/414 |
| 2005/0171115 A1 | 8/2005 | Trybulski et al. | 514/252.12 |
| 2005/0187251 A1 | 8/2005 | Mahaney et al. | 514/318 |
| 2005/0192283 A1 | 9/2005 | Trybulski et al. | 514/252.13 |
| 2005/0222148 A1 | 10/2005 | Kim et al. | 514/232.5 |

FOREIGN PATENT DOCUMENTS

| | | |
|---|---|---|
| DE | 2556474 C2 | 8/2004 |
| EP | 0 065 757 B1 | 12/1982 |
| EP | 0 135 905 A1 | 4/1985 |
| EP | 0 303 961 A1 | 2/1989 |
| EP | 0 208 235 B1 | 1/1990 |
| EP | 0 636 608 A1 | 2/1995 |
| EP | 0 636 609 A1 | 2/1995 |
| EP | 0 743 064 A1 | 11/1996 |
| EP | 1 266 659 A1 | 12/2002 |
| GB | 2 362 826 A | 5/2001 |
| WO | 91/18602 A1 | 12/1991 |
| WO | WO 93/15051 A1 | 8/1993 |
| WO | WO 95/18105 A1 | 7/1995 |
| WO | 96/05818 A1 | 2/1996 |
| WO | WO 97/15556 A1 | 5/1997 |

(Continued)

OTHER PUBLICATIONS

Acs, N. et al., "Estrogen improves impaired musculocutaneous vascular adrenergic reactivity in pharmacologically ovariectomized rats: a potential peripheral mechanism for hot flashes?", *Endocrinology*, 2001 15: 68-73.

Ahmar, M. et al., "Enzymatic resolution of methyl 2-alkyl-2-arylacetates" *Tetrahedron Lett.*, 1989, 30(50): 7053-7056.

Ainsworth, D. P. et al., "Syntheses of Heterocyclic Compounds. Part XVI. Preparative Routes to Indoles with t-Amine Substituents in the Benzene Ring," *J. Chem. Soc. [section] C: Organic* 1967, 4:315-19.

(Continued)

*Primary Examiner*—James O Wilson
*Assistant Examiner*—Erich A Leeser
(74) *Attorney, Agent, or Firm*—Thomas C. McKenzie

(57) ABSTRACT

The present invention is directed to phenylaminopropanol derivatives of formula I:

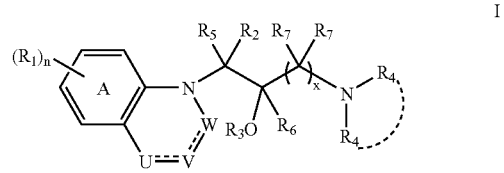

or a pharmaceutically acceptable salt thereof, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

15 Claims, 2 Drawing Sheets

FOREIGN PATENT DOCUMENTS

| WO | 97/35586 A1 | 10/1997 |
|---|---|---|
| WO | WO 98/14208 A1 | 4/1998 |
| WO | WO 98/25901 A1 | 6/1998 |
| WO | 99/44601 A1 | 9/1999 |
| WO | 99/55694 A1 | 11/1999 |
| WO | WO 00/02551 A2 | 1/2000 |
| WO | 00/59851 A1 | 10/2000 |
| WO | WO 00/66166 A1 | 11/2000 |
| WO | WO 00/66556 A1 | 11/2000 |
| WO | 01/01973 A2 | 1/2001 |
| WO | WO 01/055130 A2 | 8/2001 |
| WO | WO 01/55134 A2 | 8/2001 |
| WO | 01/72708 A2 | 10/2001 |
| WO | WO 02/02520 A2 | 1/2002 |
| WO | WO 02/22572 A2 | 3/2002 |
| WO | 02/064543 A2 | 8/2002 |
| WO | 02/078691 A1 | 10/2002 |
| WO | 03/010169 A1 | 2/2003 |
| WO | 03/037334 A1 | 5/2003 |
| WO | 03/053426 A1 | 7/2003 |
| WO | 03/077897 A1 | 9/2003 |
| WO | 2004/016272 A1 | 2/2004 |
| WO | 2004/089942 A2 | 10/2004 |

OTHER PUBLICATIONS

Baker, W.et al., "Nonpeptide renin inhibitors employing a novel 3-aza(or oxa)-2,4-dialkyl glutaric acid moiety as a P2/P3 amide bond replacement," *J. Med. Chem.* 1992, 35 (10), 1722-1734.

Barberis, C. et al., "Molecular Pharmacologoy of AVP and OT Receptors and Therapeutic Potential," *Drug News Perspect*, Jun. 1999, 12(5):279-292.

Barlow, D. H., "Venlafaxine for hot flushes," *Lancet*, Dec. 16, 2000, 356(9247): 2025-2026.

Barton, D. et al., "Hot Flashes—Aetiology and Management," *Drugs and Aging*, 2001, 18(8): 597-606.

Berendsen, H. H. G., "Effect of tibolone and raloxifene on the tail temperature of oestrogen-deficient rats," *European Journal of Pharmacology*, 2001, 419(1): 47-54.

Berendsen, H. H. G., "Hot Flushes and serotonin," *Journal of the British Menopause Society*, Mar. 2002, 8(1): 30-34.

Berendsen, H. H. G., "The role of serotonin in hot flushes," *Maturitas*, 2000, 36(3): 155-164.

Brück, K. et al., "Adaptive changes in thermoregulation and their neuropharmacological basis" In: Schönbaum E. et al. (eds.). *Thermoregulation: Physiology and Biochemistry*, New York, Pergamon Press, (1991) pp. 255-307.

Bugle, R. C., et al., "Reduction of Azanaphthalenes by Sodium Borohydride in Trifluoroacetic Acid," *Org. Chem.* 1979, 44, 1719-1720.

Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).

Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4):285-298.

Bundgaard, H., "Means to enhance penetration; Prodrugs as a means to improve the delivery of peptide drugs," *Advanced Drug Deliver Reviews*, 1992, 8, 1-38.

Cacchi, S. et al., "3-Aryl-2-Unsubstituted Indoles through the Palladium-Catalysed Reaction of o-Ethynyltrifluoroacetanilide with Aryl Iodides," *Synlett* 1997, 12:1363-1366.

Caliendo, G. et al., "Synthesis and Vasorelaxant Activity of New 1,4-benzoxazine Derivatives Potassium Channel Openers," *Bioorganic & Medicinal Chemistry*, 2002, 10:2663-2669.

Campaigne, E. et al., "Benzo[b]thiophene Derivatives. XXVII. 5-Methoxy-6-halo-3-b-acetamidoethylbenzo[b]thiophenes, Blocked Analogs of Melatonin," *J. Heterocyclic Chem.* 1983, 20, 1697-1703.

Casper, R. F. et al., "Neuroendocrinology of menopausal flushes: an hypothesis of flush mechanism," *Clinical Endocrinology*, 1985, 22: 293-312.

Cavagnol, J. C. et al., "1-Alkyl-1,2,3,4-tetrahydroquinoxalines," *J. Am. Chem. Soc.* 1947, 69, 795-799.

Clinical Trial: "Phase III Randomized Study of Medroxyprogesterone Versus Venlafaxine in Women With Symptomatic Hot Flashes", www.clinicaltrials.gov sponsored by the National Institutes of Health, Study ID Nos. CDR0000069217; NCCTG-N99C7; NCI-P02-0204, 2003, 6 pages.

Cook, G. R. et al., "Stereochemical Consequences of the Lewis Acid-Promoted 3-Aza-Cope Rearrangement of N-Alkyl-N-Allyl Enamines," *Tetrahedron*, 1994, 50(14):4105.

de Keyzer, Y, et al., "Cloning and characterization of the human V3 pituitary vasopressin receptor," *FEBS Letters*, 1994, 356:215-220.

Derick, S. et al., "[1-Deamino-4-Cyclohexylalanine] Arginine Vasopressin: A Potent and Specific Agonist for Vasopressin $V_{1b}$Receptors," *Endocrinology*, Dec. 2002, 143(12): 4655-4664.

Eliel, E. L., *Stereochemistry of Carbon Compounds*, McGraw Hill, NY (1962) Ch. 4, pp. 46-87.

El-Subbagh, H. I. et al., "Synthesis and Antitumor Activity of Some New Substituted Quinolin-4-one and 1,7-Naphthyridin-4-one Analogs," *Arch. Pharm.* 1999, 332:19-24.

Fink, G. et al., "Oestrogen and mental state," *Nature*, 1996, 383(6598): 306.

Folny, V. et al., "Pancreatic vasopressin $V_{1b}$ receptors: characterization in In-R1-G9 cells and localization in human pancreas," *Am. J. PhysioL Endocrinol. Metab.* May 7, 2003, 285: E566-E576.

Freedman, R. R. et al., "Adrenergic mechanism in menopausal hot flushes," *Obstet Gynecol*, 1990, 76:573-578.

Freedman, R. R. et al., "Clonidine raises the sweating threshold in symptomatic but not asymptomatic postmenopausal women," *Fertility & Sterility*, 2000, 74(1): 20-3.

Freedman, R. R., "Physiology of hot flashes," *American Journal of Human Biology*, 2001, 13: 453-464.

French, N., "$\alpha_2$-Adrenoceptors and $I_2$ sites in the mammalian central nervous system," *Pharmacol. Ther.*, 1995, 68(2):175-208.

Greene, T.W. and Wuts, P.G.M., *Protective Groups in Organic Synthesis* 2d. Ed., Wiley & Sons, 1991.

Gribble, G. W., "Reactions of Sodium Borohydride in Acidic Media; VI. Reduction of Indoles with Cyanoborohydride in Acetic Acid," *Synthesis*, 1977, 12:859-860.

Griebel, G. et al., "Anxiolytic- and antidepressant-like effects of the non-peptide vasopressin $V_{1b}$ Receptor antagonist, SSR149415, suggest an innovative approach for the treatment of stress-related disorders," *PNAS*, Apr. 30, 2002, 99(9): 6370-6375.

Griebel, G. et al., "The Vasopressin $V_{1b}$ Receptor as a Therapeutic Target in Stress-related Disorders," *Current Drug Targets- CNS Neurological Disorders*, 2003, 2:191-200.

Harrison, I. et al., "Nonsteroidal antiinflammatory agents. I. 6-substituted 2-naphthylacetic acids," *J. Med. Chem.* 1970, 13(2), 203-5.

Higuchi and Stella (eds.), *Prodrugs as Novel Drug Delivery Systems*, American Chemical Society (1975), pp. 1-115 and 196-223.

Jacques, J. et al., *Enantiomers, Racemates and Resolutions*, Wiley Interscience, NY (1981) pp. 251-434.

Janowsky, D. S. et al., "Desipramine: an overview," *Journal of Clinical Psychiatry*, 1984, 45(10 Pt 2): 3-9.

Katovich, M. J. et al., "Alpha-adrenergic mediation of the tail skin temperature response to naloxone in morphine-dependent rats," *Brain Research*, 1987, 426: 55-61.

Katovich, M. J. et al., *Proceedings of the Society for Experimental Biology & Medicine*, 1990, 193(2): 129-35.

Kende, A. et al., "Regioselective C-3 Alkylations of Oxindole Dianion," *Synth. Comm.* 12(1): 1-10 (1982).

Kramer et al., In: Murphy et al., 3rd *Int'l Symposium on Recent Advances in Urological Cancer Diagnosis and Treatment-Proceedings*, Paris, France: SCI: 3-7 1992.

Krogsgaard-Larsen, et al., (ed). *Design and Application of Prodrugs, Textbook of Drug Design and Development*, Chapter 5, 113-191, 1991.

Kronenberg, F. et al., "Thermoregulatory Physiology of Menopausal Hot Flashes: A Review," *Can. J. Physiol. Pharmacol.*, 1987, 65:1312-1324.

Kucerovy, A. et al., "The Reduction of Indolin-2-Ones With Sodium Bis(2-Methoxyethoxy)Aluminum Hydride," *Synth. Commun.* 1992, 22:729-733.

László, F. A. et al., "Pharmacology and Clinical Perspectives of Vasopressin Antagonists," *Pharmacol Rev*, 1991, 43(1):73-108.

Ley, S.V. et al., "Use of polymer supported reagents for clean multi-step organic synthesis: preparation of amines and amine derivatives from alcohols for use in compound library generation," *J. Chem. Soc. Perkin Trans.* 1; 15; 1998; 2239-2242.

Lolait, S. J. et al., "Extrapituitary expression of the rat V1b vasopressin receptor gene," *Neurobiology*, Jul. 1995, 92, 6783-6787.

Loprinizi, C. L. et al. "Pilot Evaluation of Venlafaxine Hydrochloride for the Therapy of Hot Flashes in Cancer Survivors," *Journal of Clinical Oncology*, Jul. 1998, 16(7): 2377-2381.

Loprinzi, C.L. et al., "Venlafaxine in management of hot flashes in survivors of breast cancer: a randomized controlled trial," *Lancet*, Dec. 16, 2000, 356(9247): 2059-2063.

Mackinnon et al., "$\alpha_2$-Adrenoceptors: more subtypes but fewer functional differences," *TIPS*, 1994, 15: 119-123.

Manning, M. et al., "Discovery, development, and some uses of vasopressin and oxytocin antagonists," *J Lab Clin Med*, Dec. 1989, 114(6):617-632.

Manov et al., "Solid-Phase Synthesis of Polyamine Spider Toxins and Correlation with the Natural Products by HPLC-MS/MS," *Helvetica Chimica Acta*, 2002, 85(9):2827-2846.

Merchenthaler et al., "The effect of estrogens and antiestrogens in a rat model for hot flush," *Maturitas*, 1998, 30(3): 307-316.

Monguzzi, R. et al., "Synthesis of new $\alpha$-hydrazinoarylacetic acids and derivatives," *Farmaco, Edizione Scientifica*, 1976, 31(8), 549-60.

Moon, S. et al., "An Efficient Conversion of Chiral $\alpha$-Amino Acids to Enantiomerically Pure 3-Amino Cyclic Amines," *Synth. Commun.* 1998, 28(21), 3919-3926.

Morin, S. M., "Atomoxetine Selectively Induces Fos Expression in the Rat Prefrontal Cortex," Presented at Society for Neuroscience Annual Meeting (SFN); Nov. 2-7, 2002, Orlando, FL.

Odle, R. et al., "Conversion of 2-Halo-*N*-allylanilines to Indoles via Palladium(0) Oxidative Addition-Insertion Reactions," *J. Org. Chem.*, 1980, 45:2709-2710.

Olagbemiro, T. O. et al., "Synthesis and Reactions of 3-Phenyl-3, 4-Quinoxalin-2(1H)-one and its Heterocyclic Analogues," *Bull Soc. Chim. Belg.* 1987, 96, 473-480.

Pacholczyk, T. et al., "Expression cloning of a cocaine-and antidepressant-sensitive human noradrenaline transporter," *Nature*, 1991, 350(6316): 350-4.

Panek, D.U. et al., "Effect of continuous intraventricular estrogen or catechol estrogen treatment on catecholamine turnover in various brain regions," *J. Pharmacol. Exp. Ther.*, 1986, 236(3), 646-652.

Prasad, P.D., et al., "Functional expression of the plasma membrane serotonin transporter but not the vesicular monoamine transporter in human placental trophoblasts and choriocarcinoma cells," *Placenta*, 1996, 17(4): 201-7.

Quella, S. K. et al., "Pilot evaluation of Venlafaxine for the treatment of hot flashes in men undergoing androgen ablation therapy for prostate cancer," *The Journal of Urology*, Jul. 1999, 162: 98-102.

Raucher, S. et al., "Synthesis of Substituted Indoles via Meerwein Arylation,"*J. Org. Chem.* 1983, 48(12):2066-2069.

*Remington's Pharmaceutical Sciences*, 17th Ed., Gennaro, A. R. (Ed.), Mack Publishing Company, Easton, PA (1985) pp. 1409-1677.

Reneric, J-Ph. et al., "Idazoxan and 8-0H-DPAT modify the behavioral effects induced by either NA, or 5-HT, or dual NA/5-HT reuptake inhibition in the rat forced swimming test," *Nueropsychopharmacology*, Apr. 2001, 24(4): 379-390.

Robertson, D. W. et al., "Dihydropyridazinone Cardiotonics: Synthesis and Inotropic Activity of 5'-(1,4,5,6-Tetrahydro-6-oxo-3-pyridazinyl)spiro[cycloalkane-1,3'-[3*H*]indol]-2'(1'*H*)-ones," *J. Med. Chem.* 1987, 30:824-829.

Rosenberg, J. et al., "Hypothesis: pathogenesis of postmenopausal hot flush," *Medical Hypotheses*, 1991, 35: 349-350.

Saito, M. et al., "Molecular cloning and characterization of rat V1b vasopressin receptor : Evidence for its expression in extra-pituitary tissues, " *Biochem. Biophys. Res. Commun.*, 1995, 212(3), 751-757.

Schmid, C. R. et al., "Synthesis of 2,3-*O*-Isopropylidene-D-glyceraldehyde in High Chemical and Optical Purity: Observations on the Development of a Practical Bulk Process," *J. Org. Chem.* 1991, 56:4056-4058.

Serradeil-Le Gal, C. et al., "Functional and Pharmacological Characterization of the First Specific Agonist and Antagonist for the V1b Receptor in Mammals," *Stress* Sep. 2003, 6(3):199-206.

Serradeil-Le Gal, C. et al., "Nonpeptide vasopressin receptor antagonists: development of selective and orally active $V_{1a}$, $V_2$ and $V_{1b}$ receptor ligands," *Progress in Brain Research*, 2002, 139:197-210.

Serradeil-Le Gal, et al., "Biological and Pharmacological Properties of SR 49059, a New, Potent, Nonpeptide Antagonist of Rat and Human Vasopressin $V_{1a}$ Receptors," *J Clin Invest*, 1993 92(1):224-231.

Serradeil-Le Gal. C. et al., "Characterization of (2S,4R)-1-[5-Chloro-1-[(2,4-dimethyoxyphenyl)sulfonyl]-3-(2-methoxyphenyl)-2-oxo-2,3-dihydro-1H-indo1-3-yl]-4-hydroxy-N,N-dimethyl-2-pyrrolidine carboxamide (SSR149415), a Selective and Orally Active Vasopressin $V_{1b}$ Receptor Antagonist,"*J Pharmacol Exp Ther*, 2002, 300(3):1122-30.

Sharpless, et. al., "Asymmetric Epoxidation of Allyl Alcohol: Efficient Routes to Homochiral β-Adrenergic Blocking Agents," *J. Org. Chem.* 1986, 51, 3710-3712.

Shaw, C. R., "The perimenopausal hot flash: epidemiology, physiology, and treatment," *Nurse Practitioner*, Mar. 1997, 22: 55-56, 61-66.

Stearns, V. et al., "A pilot trial assessing the efficacy of paroxetine hydrochloride (Paxil) in controlling hot flashes in breast cancer survivors," *Ann Oncol.*, 2000, 11:17-22.

Stearns, V. et al., "Hot flushes," *Lancet*, Dec. 7, 2002, 360(9348): 1851-1861.

Stearns,V. et al., "Paroxetine controlled release in the treatment of menopausal hot flashes," *JAMA*, 2003, 289:2827-2834.

Sugimoto, T. et al., "Molecular Cloning and Functional Expression of a cDNA Encoding the Human $V_{1b}$ Vasopressin Receptor," *J. Biol. Chem.*, Oct. 28, 1994, 269(43) : 27088-27092.

Tahara, A. et al., "Pharmacological profile of YM087, A Novel Potent Nonpeptide Vasopressin $V_{1A}$ and $V_2$ Receptor Atagonist, in Vitro and in Vivo," *JPET*, 1997, 282(1):301-308.

Ventura, M. A. et al., "Gene and cDNA cloning and characterization of the mouse V3/V1b pituitary vasopressin receptor," *Journal of Molecular Endocrinology*, 1999, 22, 251-260.

Waldinger et al., "Treatment of hot flushes with mirtazapine: four case reports," *Maturitas*, 2000, 36(3): 165-168.

Wersinger, S. R. et al., "Vasopressin V1b receptor knockout reduces aggressive behavior in male mice," *Mol Psychiatry*, 2002, 7:975-984.

Wheeler, K. W., "Some 2-Substituted 2H-1,4-Benzoxazin-3(4H)-ones," *J. Med. Pharm. Chem.* 1962, 5:1378-1383.

Widder, et al. (ed.), *Methods in Enzymology*, vol. 112, Academic Press (1985), pp. 309-396.

Wilen, S.H. *Tables of Resolving Agents and Optical Resolutions*, pp. 268-298, E.L. Eliel, Ed., University of Notre Dame Press, Notre Dame, IN 1972.

Wilen, S.H., et al., "Strategies in optical resolutions," *Tetrahedron*, 33:2725-2736, 1977.

Wu, X-Y. et al., " Highly Enantioselective Epoxidation of $\alpha,\beta$-Unsaturated Esters by Chiral Dioxirane," *J. Am. Chem. Soc.*, 2002, 124, 8792-8793.

Yamamura, Y. et al., "Characterization of a novel aquaretic agent, OPC-31260, as an orally effective, nonpeptide vasopressin $V_2$ receptor antagonist," *Br J Pharmacol*, (1992),105(4):787-791.

Yang, D. et al., "Epoxidation of Olefins Using Methyl(trifluoromethyl)dioxirane Generated in Situ," *J. Org. Chem.* 1995, 60, 3887-3889.

Zhang, W. et al., "Synergistic Effects of Olanzapine and Other Antipsychotic Agents in Combination with Fluoxetine on Norepinephrine and Dopamine Release in Rat Prefrontal Cortex," *Neuropsychopharmacology*, 2000, 23(3): 250-262.

Zhang, Z. et al., "A General Method for the Preparation of 4- and 6-Azaindoles," *J. Org. Chem.*, 2002, 67:2345-2347.

Chemical Abstracts Service; 1997, Elker, A. et al., "Aminolysis of derivatives of trans-3-phenylglycidic acid with aromatic amines, IV" XP002338398 retrieved from STN Database accession No. 1979:420066 abstract & Archiv Der Pharmazie ((Weinheim, Germany), 312(1), 26-34, (1979).

* cited by examiner

PHENYLAMINOPROPANOL DERIVATIVES AND METHODS OF THEIR USE

CROSS REFERENCE TO RELATED APPLICATIONS

This application is a divisional of U.S. application Ser. No. 11/091,291, filed on Mar. 28, 2005, which claims the benefit of U.S. application Ser. No. 60/557,831 filed Mar. 30, 2004 and U.S. application Ser. No. 60/569,861 filed May 11, 2004, the entire disclosures of which are herein incorporated by reference.

FIELD OF THE INVENTION

The present invention relates to phenylaminopropanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., $3^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, et al., Lancet, 2000, 356(9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," Can. J. Physiol. Pharmacol., 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al., Lancet, 2000, 356:2059-2063; Stearns et al., JAMA, 2003, 289:2827-2834) compared to doses used to treat the behavioral aspects of depression. The interplay of the CNS/PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., Maturitas, 2000, 36(3): 165-168).

It has been reported that $\alpha_2$-adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the adrenergic$_{\alpha2}$ receptors, i.e., are $\alpha_{2A}$, $\alpha_{2B}$, $\alpha_{2C}$ and $\alpha_{2D}$ (Mackinnon et al., TIPS, 1994, 15: 119;

French, *Pharmacol. Ther.*, 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al., *Proceedings of the Society for Experimental Biology & Medicine,* 1990, 193(2): 129-35, Freedman et al., *Fertility & Sterility,* 2000, 74(1): 20-3). Clonidine has been used to treat hot flush. However, using such treatment is associated with a number of undesired side effects caused by high doses necessary to abate hot flash described herein and known in the related arts.

Given the complex multifaceted nature of thermoregulation and the interplay between the CNS and PNS in maintaining thermoregulatory homeostasis, multiple therapies and approaches can be developed to target vasomotor symptoms. The present invention focuses on novel compounds and compositions containing these compounds directed to these and other important uses.

SUMMARY OF THE INVENTION

The present invention is directed to phenylaminopropanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the invention is directed to compounds of formula I:

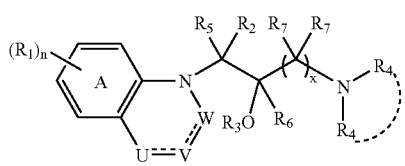

or a pharmaceutically acceptable salt thereof;
wherein:
the dotted line represents an optional double bond between U and V or V and W;
U is, independently, O, S, SO, $SO_2$, C=O, N, $NR_3$, or $C(R_8)_2$;
W is CH, $CH_2$, or C=O;
provided that when W is $CH_2$, U is not $C(R_8)_2$;
V is $C(R_8)$, $C(R_8)_2$, O, or $N(R_8)$;
$R_1$ is, independently at each occurrence, alkyl, alkoxy, halo, $CF_3$, $OCF_3$, arylalkyloxy substituted with 0-3 $R_9$, aryloxy substituted with 0-3 $R_9$, aryl substituted with 0-3 $R_9$, heteroaryl substituted with 0-3 $R_9$, hydroxy, alkanoyloxy, nitro, nitrile, alkenyl, alkynyl, alkylsulfoxide, phenylsulfoxide substituted with 0-3 $R_9$, alkylsulfone, phenylsulfone substituted with 0-3 $R_9$, alkylsulfonamide, phenylsulfonamide substituted with 0-3 $R_9$, heteroaryloxy substituted with 0-3 $R_9$, heteroarylmethyloxy substituted with 0-3 $R_9$, alkylamido, or phenylamido substituted with 0-3 $R_9$; or two adjacent $R_1$ also represent methylenedioxy;

$R_2$ is aryl substituted with 0-3 $R_1$ or heteroaryl substituted with 0-3 $R_1$;

$R_3$ is H, $C_1$-$C_4$ alkyl substituted with 0-3 $R_1$, $C_3$-$C_6$ cycloalkyl, or phenyl substituted with 0-3 $R_1$;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl, or both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$-$C_4$ alkyl, F, or $CF_3$;

$R_5$ is H or $C_1$-$C_4$ alkyl;

$R_6$ is H or $C_1$-$C_4$ alkyl;

$R_7$ is, independently at each occurrence, H, or $C_1$-$C_4$ alkyl, or $R_7$ and $R_4$ together with the nitrogen to which $R_4$ is attached form a nitrogen-containing ring containing 3-6 carbon atoms;

$R_8$ is, independently at each occurrence, H, $C_1$-$C_4$ alkyl, $C_3$-$C_6$ heteroalkyl, or aryl substituted with 0-3 $R_1$;

$R_9$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_9$ also represent methylenedioxy;

n is an integer from 0 to 4;

x is an integer from 1 to 2; and wherein 1-3 carbon atoms in ring A may optionally be replaced with N.

In yet other embodiments, the present invention is directed to compositions, comprising:
a. at least one compound of formula I; and
b. at least one pharmaceutically acceptable carrier.

In another embodiment, the present invention is directed to methods for treating or preventing a condition ameliorated by monoamine reuptake in a subject in need thereof, comprising the step of:
administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In another embodiment, the present invention is directed to methods for treating or preventing vasomotor symptoms in a subject in need thereof, comprising the step of:
administering to said subject an effective amount of at least one compound of formula I or pharmaceutically acceptable salt thereof.

In yet another embodiment, the present invention is directed to methods for treating or preventing a depression disorder in a subject in need thereof, comprising the step of:
administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:

administering to said subject an effective amount of at least one compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of at least one compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of at least one compound of formula I or pharmaceutically acceptable salt thereof.

In another embodiment, the present invention is directed to methods for treating or preventing fibromyalgia syndrome in a subject in need thereof, comprising the step of:

administering to said subject an effective amount of at least one compound of formula I or pharmaceutically acceptable salt thereof.

BRIEF DESCRIPTION OF THE DRAWINGS

The invention can be more fully understood from the following detailed description and the accompanying drawings that form a part of this application.

DETAILED DESCRIPTION OF THE INVENTION

Figure 1:
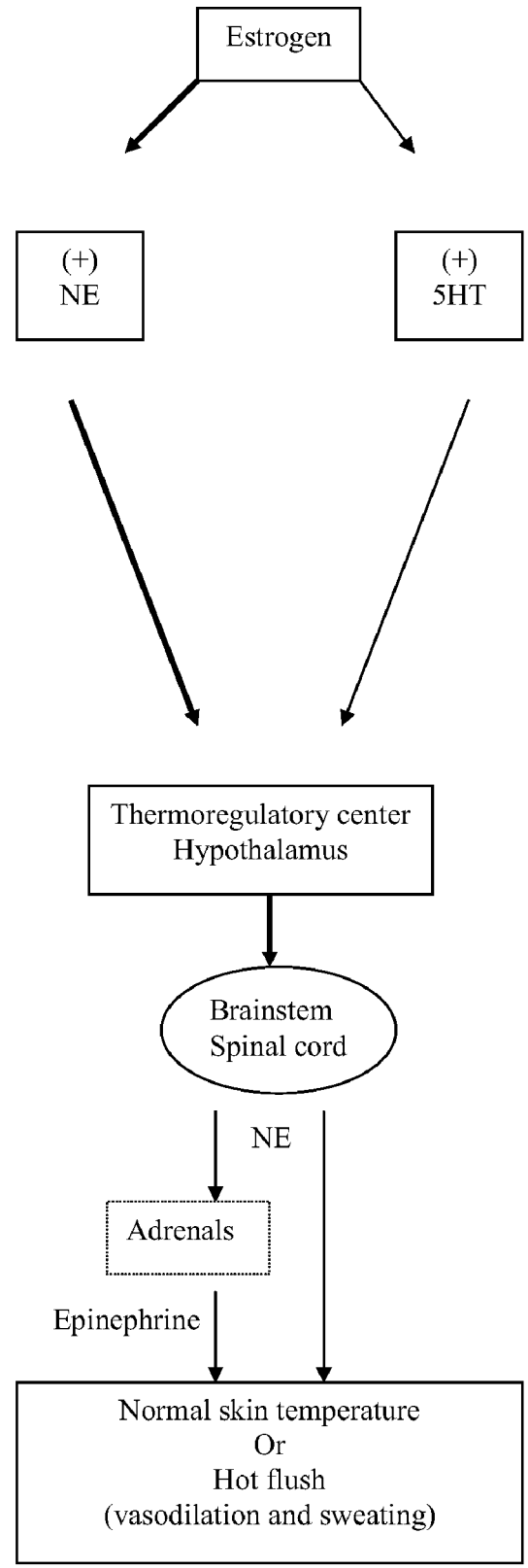
FIG. 1 is an overview of estrogen action on norepinephrine/serotonin mediated thermoregulation.

The present invention is directed to phenylaminopropanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "ED$_{50}$ value" means dose which results in 50% alleviation of the observed condition or effect (50% mean maximum endpoint).

"Norepinephrine transporter" is abbreviated NET.
"Human norepinephrine transporter" is abbreviated hNET.
"Serotonin transporter" is abbreviated SERT.
"Human serotonin transporter" is abbreviated hSERT.
"Norepinephrine reuptake inhibitor" is abbreviated NRI.
"Selective norepinephrine reuptake inhibitor" is abbreviated SNRI.
"Serotonin reuptake inhibitor" is abbreviated SRI.
"Selective serotonin reuptake inhibitor" is abbreviated SSRI.
"Norepinephrine" is abbreviated NE.
"Serotonin is abbreviated 5-HT.
"Subcutaneous" is abbreviated sc.
"Intraperitoneal" is abbreviated ip.
"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

The term "effective amount," as used herein, refers to an amount effective, at dosages, and for periods of time necessary, to achieve the desired result with respect to prevention or treatment of vasomotor symptoms, depression disorders, sexual dysfunction, or pain. In particular, with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to depression disorders, sexual dysfunction, and pain, the compounds of the present invention are administered at a dosage and for a time such that there is the prevention, alleviation, or elimination of the symptom or condition.

For example, for an afflicted patient, compounds of formula I, or a pharmaceutically acceptable salt thereof, may be administered, preferably, at a dosage of from about 0.1 mg/day to about 500 mg/day, dosed one or two times daily, more preferably from about 1 mg/day to about 200 mg/day and most preferably from about 1 mg/day to 100 mg/day for a time sufficient to reduce and/or substantially eliminate the number and/or severity of hot flushes or symptom or condition of the depression disorder, sexual dysfunction, or pain.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The terms "component", "drug" or "pharmacologically active agent" or "active agent" or "medicament" are used interchangeably herein to refer to a compound or compounds or composition of matter which, when administered to an organism (human or animal) induces a desired pharmacologic and/or physiologic effect by local and/or systemic action.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

As used herein, the term "inhibitor" refers to any agent that inhibits, suppresses, represses, or decreases a specific activity, such as serotonin reuptake activity or the norepinephrine reuptake activity.

The term "inhibitor" is intended to comprise any compound, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the compounds of formula I may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor symptoms, depression disorders, sexual dysfunction, or pain, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316.

"Side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry*, 1984, 45(10 Pt 2): 3-9).

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms being preferred, and with from about 1 to about 4 carbon atoms, herein referred to as "lower alkyl", being more preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

"Heteroalkyl," as used herein, refers to a substituent of the general formula (alkyl-X)$_n$-alkyl-, where each "alkyl" is independently as defined above, "X" is a sulfur, oxygen, or N heteroatom-containing moiety, and n is 1-4, preferably one. Heteroalkyl groups include, but are not limited to, methoxymethyl, ethoxyethyl, methoxyethyl, methylsulfanylmethyl, ethylsulfanylethyl, methylsulfanylethyl, methylaminoethyl, ethylaminoethyl, and methylaminoethyl.

"Perfluorinated alkyl," as used herein, refers to an alkyl, as defined above, in which the hydrogens directly attached to the carbon atoms are completely replaced by fluorine.

"Alkenyl," as used herein, refers to an alkyl group of at least two carbon atoms having one or more double bonds, wherein alkyl is as defined herein. Alkenyl groups can be optionally substituted.

"Alkynyl," as used herein, refers to an alkyl group of at least two carbon atoms having one or more triple bonds, wherein alkyl is as defined herein. Alkynyl groups can be optionally substituted.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Heteroaryl," as used herein, refers to an optionally substituted, mono-, di-, tri-, or other multicyclic aromatic ring system that includes at least one, and preferably from 1 to about 4 heteroatom ring members selected from sulfur, oxygen and nitrogen. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinyl. Also included are fused ring and spiro compounds containing, for example, the above heterocycles.

"Alkoxy," as used herein, refers to the group R—O— where R is an alkyl group as defined herein.

"Aryloxy," as used herein, refers to the group R—O— where R is an aryl group, as defined herein.

"Heteroaryloxy," as used herein, refers to the group R—O— where R is a heteroaryl group, as defined herein.

"Alkanoyloxy," as used herein, refers to the group R—C(=O)—O— where R is an alkyl group of 1 to 5 carbon atoms.

"Alkylsulfoxide," as used herein, refers to as used herein, refers to —S(=O)—R, where R is alkyl, as defined above.

"Alkylsulfone," as used herein, refers to —S(=O)$_2$—R, where R is alkyl, as defined above.

"Alkylsulfonamide," as used herein, refers to —NR—S(=O)$_2$—R, where each R is independently, alkyl, as defined above or the NR part may also be NH.

"Phenylsulfonamide," as used herein, refers to —NR—S(=O)$_2$-phenyl, where R is H or alkyl, as defined above.

"Heteroarylmethyloxy," as used herein, refers to —OCH$_2$—R, where R is heteroaryl, as defined above.

"Alkylamido," as used herein, refers to —NR—C(=O)—R, where each R is independently, alkyl, as defined above, or the NR part may also be NH.

"Phenylamido," as used herein, refers to —NR—C(=O)-phenyl, where R is H or alkyl, as defined above.

"Halo," as used herein, refers to chloro, bromo, fluoro, and iodo.

In one embodiment, the invention is directed to compounds of formula I:

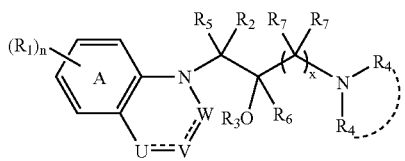

or a pharmaceutically acceptable salt thereof;
wherein:
the dotted line represents an optional double bond between U and V or V and W;
U is, independently, O, S, SO, SO$_2$, C=O, N, NR$_3$, or C(R$_8$)$_2$;
W is CH, CH$_2$, or C=O;
provided that when W is CH$_2$, U is not C(R$_8$)$_2$;
V is C(R$_8$), C(R$_8$)$_2$, O, or N(R$_8$);

$R_1$ is, independently at each occurrence, alkyl, alkoxy, halo, $CF_3$, $OCF_3$, arylalkyloxy substituted with 0-3 $R_9$, aryloxy substituted with 0-3 $R_9$, aryl substituted with 0-3 $R_9$, heteroaryl substituted with 0-3 $R_9$, hydroxy, alkanoyloxy, nitro, nitrile, alkenyl, alkynyl, alkylsulfoxide, phenylsulfoxide substituted with 0-3 $R_9$, alkylsulfone, phenylsulfone substituted with 0-3 $R_9$, alkylsulfonamide, phenylsulfonamide substituted with 0-3 $R_9$, heteroaryloxy substituted with 0-3 $R_9$, heteroarylmethyloxy substituted with 0-3 $R_9$, alkylamido, or phenylamido substituted with 0-3 $R_9$; or two adjacent $R_1$ also represent methylenedioxy;

$R_2$ is aryl substituted with 0-3 $R_1$ or heteroaryl substituted with 0-3 $R_1$;

$R_3$ is H, $C_1$-$C_4$ alkyl substituted with 0-3 $R_1$, $C_3$-$C_6$ cycloalkyl, or phenyl substituted with 0-3 $R_1$;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl, or both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$-$C_4$ alkyl, F, or $CF_3$;

$R_5$ is H or $C_1$-$C_4$ alkyl;

$R_6$ is H or $C_1$-$C_4$ alkyl;

$R_7$ is, independently at each occurrence, H, or $C_1$-$C_4$ alkyl, or $R_7$ and $R_4$ together with the nitrogen to which $R_4$ is attached form a nitrogen-containing ring containing 3-6 carbon atoms;

$R_8$ is, independently at each occurrence, H, $C_1$-$C_4$ alkyl, $C_3$-$C_6$ heteroalkyl, or aryl substituted with 0-3 $R_1$;

$R_9$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_9$ also represent methylenedioxy;

n is an integer from 0 to 4;

x is an integer from 1 to 2; and wherein 1-3 carbon atoms in ring A may optionally be replaced with N.

The dotted line in the ring fused to ring A represents either an optional double bond between U and V or between V and W. The dotted line between the two $R_4$ groups represents an optional heterocyclic ring of 4 to 6 ring atoms that may be formed between the two $R_4$ groups, together with the nitrogen through which they are attached.

In certain preferred embodiments of compounds of formula I, U is O. In certain other preferred embodiments, U is S. In certain other preferred embodiments, U is SO. In certain other preferred embodiments, U is $SO_2$. In certain other preferred embodiments, U is C=O. In certain other preferred embodiments, U is NH. In certain other preferred embodiments, U is $NR_3$. In certain other preferred embodiments, U is $CH_2$.

In certain preferred embodiments of compounds of formula I, W is CH. In certain other preferred embodiments, W is $CH_2$. In certain other preferred embodiments, W is C=O.

In certain preferred embodiments of compounds of formula I, V is $C(R_8)$, especially CH. In certain other preferred embodiments, V is $C(R_8)_2$, especially $CH_2$. In certain other preferred embodiments, V is O. In certain other preferred embodiments, V is $N(R_8)$, especially NH.

In certain preferred embodiments of compounds of formula I, $R_1$ is, independently at each occurrence, alkyl, preferably $C_1$-$C_4$ alkyl, more preferably methyl. In certain other preferred embodiments, $R_1$ is, independently at each occurrence, alkoxy. In certain other preferred embodiments of compounds, $R_1$ is, independently at each occurrence, halo, preferably F or Cl. In certain other preferred embodiments, $R_1$ is, independently at each occurrence, $CF_3$. In certain other preferred embodiments, $R_1$ is, independently at each occurrence, $OCF_3$. In certain other preferred embodiments, $R_1$ is, independently at each occurrence, benzyloxy substituted with 0-3 $R_1$. In certain other preferred embodiments, $R_1$ is, independently at each occurrence, aryloxy substituted with 0-3 $R_1$. In certain other preferred embodiments, $R_1$ is, independently at each occurrence, aryl substituted with 0-3 $R_1$. In certain other preferred embodiments, $R_1$ is, independently at each occurrence, heteroaryl substituted with 0-3 $R_1$. In certain other preferred embodiments, $R_1$ is, independently at each occurrence, hydroxy. In certain other preferred embodiments, $R_1$ is, independently at each occurrence, alkanoyloxy. In certain other preferred embodiments, $R_1$ is, independently at each occurrence, methylenedioxy. In certain other preferred embodiments, $R_1$ is, independently at each occurrence, nitro. In certain other preferred embodiments, $R_1$ is, independently at each occurrence, nitrile. In certain other preferred embodiments, $R_1$ is, independently at each occurrence, alkenyl. In certain other preferred embodiments, $R_1$ is, independently at each occurrence, alkynyl. In certain other preferred embodiments, $R_1$ is, independently at each occurrence, alkylsulfoxide. In certain other preferred embodiments, $R_1$ is, independently at each occurrence, phenylsulfoxide substituted with 0-3 $R_1$. In certain other preferred embodiments, $R_1$ is, independently at each occurrence, alkylsulfone. In certain other preferred embodiments, $R_1$ is, independently at each occurrence, phenylsulfone substituted with 0-3 $R_1$. In certain other preferred embodiments, $R_1$ is, independently at each occurrence, alkylsulfonamide. In certain other preferred embodiments, $R_1$ is, independently at each occurrence, phenylsulfonamide substituted with 0-3 $R_1$. In certain other preferred embodiments, $R_1$ is, independently at each occurrence, heteroaryloxy substituted with 0-3 $R_1$. In certain other preferred embodiments, $R_1$ is, independently at each occurrence, heteroarylmethyloxy substituted with 0-3 $R_1$. In certain other preferred embodiments, $R_1$ is, independently at each occurrence, alkylamido. In certain other preferred embodiments, $R_1$ is, independently at each occurrence, phenylamido substituted with 0-3 $R_1$.

In certain preferred embodiments of compounds of formula I, $R_2$ is aryl substituted with 0-3 $R_1$, preferably substituted with no $R_1$. In certain preferred embodiments, $R_2$ is naphthyl substituted with 0-3 $R_1$, preferably substituted with no $R_1$. In certain preferred embodiments, $R_2$ is heteroaryl substituted with 0-3 $R_1$, preferably substituted with no $R_1$.

In certain preferred embodiments of compounds of formula I, $R_3$ is H. In certain other preferred embodiments, $R_3$ is $C_1$-$C_4$ alkyl, preferably $C_1$ alkyl. In certain other preferred embodiments, $R_3$ is $C_3$-$C_6$ alkyl, preferably $C_5$-$C_6$ alkyl. In certain other preferred embodiments, $R_3$ is phenyl substituted with 0-3 $R_1$, especially phenyl.

In certain preferred embodiments of compounds of formula I, $R_4$ is, independently at each occurrence, H. In certain preferred embodiments, $R_4$ is, independently at each occurrence, $C_1$-$C_4$ alkyl, preferably $C_1$-$C_3$ alkyl, more preferably methyl, ethyl, or isopropyl. In certain preferred embodiments of compounds of formula I, $R_4$ is, independently at each occurrence, benzyl. In certain preferred embodiments, $R_4$ is, independently at each occurrence, heteroarylmethyl. In certain preferred embodiments, $R_4$ is, independently at each occurrence, cycloheptyl methyl, cyclohexyl methyl, cyclopentyl methyl, or cyclobutyl methyl.

In certain preferred embodiments of compounds of formula I, both $R_4$ groups, together with the nitrogen through which they are attached, form a heterocyclic ring of 4 to 6 ring atoms, where one carbon may be optionally replaced with N, O, S, or $SO_2$, and where any carbon ring atom may be optionally substituted with $C_1$-$C_4$ alkyl, F, or $CF_3$. In certain more preferred embodiments, both $R_4$ groups, together with the nitrogen through which they are attached, form a pyridine, piperidine, piperazine, or morpholine ring.

In certain preferred embodiments of compounds of formula I, $R_5$ is, independently at each occurrence, H. In certain preferred embodiments, $R_5$ is, independently at each occurrence, $C_1$-$C_4$ alkyl, preferably $C_1$-$C_3$ alkyl, more preferably methyl, ethyl, or isopropyl.

In certain preferred embodiments of compounds of formula I, $R_6$ is, independently at each occurrence, H. In certain preferred embodiments, $R_6$ is, independently at each occurrence, $C_1$-$C_4$ alkyl, preferably $C_1$-$C_3$ alkyl, more preferably methyl, ethyl, or isopropyl.

In certain preferred embodiments of compounds of formula I, $R_7$ is, independently at each occurrence, H. In certain preferred embodiments, $R_7$ is, independently at each occurrence, $C_1$-$C_4$ alkyl, preferably $C_1$-$C_3$ alkyl, more preferably methyl, ethyl, or isopropyl. In certain preferred embodiments of compounds of formula I, $R_7$ and $R_4$ together with the nitrogen to which $R_4$ is attached form a nitrogen-containing ring containing 3-6 carbon atoms, especially, pyrrolidinyl, pyrrolyl, piperidinyl, pyridinyl, azepanyl, and azepinyl.

In certain preferred embodiments of compounds of formula I, $R_8$ is, independently at each occurrence, H. In certain preferred embodiments, $R_8$ is, independently at each occurrence, $C_1$-$C_4$ alkyl, preferably $C_1$-$C_3$ alkyl, more preferably methyl, ethyl, or isopropyl. In certain preferred embodiments of compounds of formula I, $R_8$ is, independently at each occurrence, $C_3$-$C_6$ heteroalkyl, preferably methoxymethyl, ethoxyethyl, methoxyethyl, methylsulfanylmethyl, ethylsulfanylethyl, methylsulfanylethyl, methylaminoethyl, ethylaminoethyl, and methylaminoethyl. In certain preferred embodiments of compounds of formula I, $R_8$ is, independently at each occurrence, aryl substituted with 0-3 $R_1$, especially phenyl, tolyl, and xylyl.

In certain preferred embodiments of compounds of formula I, $R_9$ is, independently at each occurrence, alkyl, preferably $C_1$-$C_6$ alkyl, $C_1$-$C_4$ alkyl, preferably $C_1$-$C_3$ alkyl, more preferably methyl, ethyl, or isopropyl. In certain preferred embodiments of compounds of formula I, $R_9$ is, independently at each occurrence, alkoxy. In certain preferred embodiments of compounds of formula I, $R_9$ is, independently at each occurrence, halo. In certain preferred embodiments of compounds of formula I, $R_9$ is, independently at each occurrence, $CF_3$. In certain preferred embodiments of compounds of formula I, $R_9$ is, independently at each occurrence, $OCF_3$. In certain preferred embodiments of compounds of formula I, $R_9$ is, independently at each occurrence, hydroxy. In certain preferred embodiments of compounds of formula I, $R_9$ is, independently at each occurrence, alkanoyloxy. In certain preferred embodiments of compounds of formula I, $R_9$ is, independently at each occurrence, methylenedioxy. In certain preferred embodiments of compounds of formula I, $R_9$ is, independently at each occurrence, nitro. In certain preferred embodiments of compounds of formula I, $R_9$ is, independently at each occurrence, nitrile. In certain preferred embodiments of compounds of formula I, $R_9$ is, independently at each occurrence, alkenyl. In certain preferred embodiments of compounds of formula I, $R_9$ is, independently at each occurrence, alkynyl. In certain preferred embodiments of compounds of formula I, $R_9$ is, independently at each occurrence, alkylsulfoxide. In certain preferred embodiments of compounds of formula I, $R_9$ is, independently at each occurrence, alkylsulfone. In certain preferred embodiments of compounds of formula I, $R_9$ is, independently at each occurrence, alkylsulfonamido. In certain preferred embodiments of compounds of formula I, $R_9$ is, independently at each occurrence, alkylamido.

In certain preferred embodiments of compounds of formula I, n is an integer from 0 to 3. More preferably, n is 0 to 2. Even more preferably, n is 0 to 1. Yet more preferably, n is 0.

In certain preferred embodiments of compounds of formula I, x is an integer from 1 to 2. More preferably, x is 1.

In certain preferred embodiments of compounds of formula I, 1-2 carbon atoms in ring A may optionally be replaced with N. In certain preferred embodiments, one carbon atom in ring A may optionally be replaced with N. In certain preferred embodiments, no carbon atoms in ring A are replaced with N.

Preferred compounds of formula I include:
1-(2,3-dihydro-4H-1,4-benzoxazin-4-yl)-3-(methylamino)-1-phenylpropan-2-ol;
3-(methylamino)-1-(4-methyl-3,4-dihydroquinoxalin-1(2H)-yl)-1-phenylpropan-2-ol;
3-(methylamino)-1-phenyl-1-[4-(2,2,2-trifluoroethyl)-3,4-dihydroquinoxalin-1(2H)-yl]propan-2-ol;
1-(6-chloro-2,3-dihydro-4H-1,4-benzoxazin-4-yl)-1-(3,5-difluorophenyl)-3-(methylamino)propan-2-ol;
1-(3-fluorophenyl)-3-(methylamino)-1-(2-methyl-2,3-dihydro-4H-1,4-benzoxazin-4-yl)propan-2-ol;
1-(6-chloro-2,3-dihydro-4H-1,4-benzoxazin-4-yl)-3-(methylamino)-1-phenylpropan-2-ol;
3-(methylamino)-1-(6-methyl-2,3-dihydro-4H-1,4-benzoxazin-4-yl)-1-phenylpropan-2-ol;
1-(6-chloro-2,3-dihydro-4H-1,4-benzoxazin-4-yl)-3-(methylamino)-1-phenylpropan-2-ol;
1-(6-chloro-2,3-dihydro-4H-1,4-benzoxazin-4-yl)-3-(methylamino)-1-phenylpropan-2-ol;
1-(6-chloro-2,3-dihydro-4H-1,4-benzoxazin-4-yl)-1-(3-fluorophenyl)-3-(methylamino)propan-2-ol;
1-(2,2-dimethyl-2,3-dihydro-4H-1,4-benzoxazin-4-yl)-1-(3-fluorophenyl)-3-(methylamino)propan-2-ol;
1-(2,2-dimethyl-2,3-dihydro-4H-1,4-benzoxazin-4-yl)-3-(methylamino)-1-phenylpropan-2-ol;
1-(2,3-dihydro-4H-1,4-benzothiazin-4-yl)-1-(3-fluorophenyl)-3-(methylamino)propan-2-ol;
1-(3-fluorophenyl)-3-(methylamino)-1-(2-phenyl-2,3-dihydro-4H-1,4-benzoxazin-4-yl)propan-2-ol;
1-(3-fluorophenyl)-3-(methylamino)-1-[2-phenyl-2,3-dihydro-4H-1,4-benzoxazin-4-yl]propan-2-ol;
1-(3-fluorophenyl)-3-(methylamino)-1-[2-phenyl-2,3-dihydro-4H-1,4-benzoxazin-4-yl]propan-2-ol; and
pharmaceutically acceptable salts thereof, particularly dihydrochloride salts thereof.

Particularly preferred compounds of formula I include:
(1RS,2SR)-1-(2,3-dihydro-4H-1,4-benzoxazin-4-yl)-3-(methylamino)-1-phenylpropan-2-ol;
(1S*,2R*)-3-(methylamino)-1-(4-methyl-3,4-dihydroquinoxalin-1(2H)-yl)-1-phenylpropan-2-ol;
(1S*,2R*)-3-(methylamino)-1-phenyl-1-[4-(2,2,2-trifluoroethyl)-3,4-dihydroquinoxalin-1(2H)-yl]propan-2-ol;
(1S,2R)-1-(6-chloro-2,3-dihydro-4H-1,4-benzoxazin-4-yl)-1-(3,5-difluorophenyl)-3-(methylamino)propan-2-ol;

(1S,2R)-1-(3-fluorophenyl)-3-(methylamino)-1-(2-methyl-2,3-dihydro-4H-1,4-benzoxazin-4-yl)propan-2-ol;
(1S*,2R*)-1-(6-chloro-2,3-dihydro-4H-1,4-benzoxazin-4-yl)-3-(methylamino)-1-phenylpropan-2-ol;
(1S*,2R*)-3-(methylamino)-1-(6-methyl-2,3-dihydro-4H-1,4-benzoxazin-4-yl)-1-phenylpropan-2-ol;
(1S,2R)-1-(6-chloro-2,3-dihydro-4H-1,4-benzoxazin-4-yl)-3-(methylamino)-1-phenylpropan-2-ol;
(1R,2S)-1-(6-chloro-2,3-dihydro-4H-1,4-benzoxazin-4-yl)-3-(methylamino)-1-phenylpropan-2-ol;
(1S,2R)-1-(6-chloro-2,3-dihydro-4H-1,4-benzoxazin-4-yl)-1-(3-fluorophenyl)-3-(methylamino)propan-2-ol;
(1S,2R)-1-(2,2-dimethyl-2,3-dihydro-4H-1,4-benzoxazin-4-yl)-1-(3-fluorophenyl)-3-(methylamino)propan-2-ol;
(1S,2R)-1-(2,2-dimethyl-2,3-dihydro-4H-1,4-benzoxazin-4-yl)-3-(methylamino)-1-phenylpropan-2-ol;
(1S,2R)-1-(2,3-dihydro-4H-1,4-benzothiazin-4-yl)-1-(3-fluorophenyl)-3-(methylamino)propan-2-ol;
(1S,2R)-1-(3-fluorophenyl)-3-(methylamino)-1-(2-phenyl-2,3-dihydro-4H-1,4-benzoxazin-4-yl)propan-2-ol;
(1S,2R)-1-(3-fluorophenyl)-3-(methylamino)-1-[(2R)-2-phenyl-2,3-dihydro-4H-1,4-benzoxazin-4-yl]propan-2-ol;
(1S,2R)-1-(3-fluorophenyl)-3-(methylamino)-1-[(2S)-2-phenyl-2,3-dihydro-4H-1,4-benzoxazin-4-yl]propan-2-ol; and
pharmaceutically acceptable salts thereof, particularly dihydrochloride salts thereof.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron,* 33:2725 (1977); Eliel, E. L. *Stereochemistry of Carbon Compounds*, (McGraw-Hill, NY, 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula I. "Prodrug," as used herein, means a compound which is convertible in vivo by metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews,* 1992, 8:1-38, Bundgaard, *J. of Pharmaceutical Sciences,* 1988, 77:285 et seq.; and Higuchi and Stella (eds.) *Prodrugs as Novel Drug Delivery Systems*, American Chemical Society (1975).

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature.

The compounds of this invention contain chiral centers, providing various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature.

The compounds of this invention contain chiral centers, providing various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

In accordance with this invention, compounds of formula I are produced by the following reaction schemes (Schemes I to VII). Depending on the desired diastereomer, the compounds are prepared via different synthetic routes (diastereomer A—Schemes I and III, and diastereomer B—Scheme IV). If it is desired to synthesize compounds of formula I-a, they can be prepared from compounds of formula 18 and 19 in three steps beginning with a regio- and stereo-selective ring opening of an epoxide of formula 19 with an appropriately substituted compound of formula 18 to produce compounds of formula 20 (Scheme I). Any conventional method for the regio- and stereo-selective opening of an epoxide can be utilized for this conversion. In accordance with the preferred embodiment of this invention, compounds of formula 18 are heated with compounds of formula 19 at temperatures from about 120° C. to about 150° C. in the absence of solvent to afford compounds of formula 20. Compounds of formula 21 can be formed from compounds of formula 20 via direct amidation with an appropriate amine. Any conventional method for direct conversion of an ester to an amide can be utilized for this conversion. In accordance with the preferred embodiment of this invention, compounds of formula 20 are heated in a sealed tube at temperatures between about 50° C. to about 100° C. with an excess of alcoholic amine to form compounds of formula 21 which can be reduced to form compounds of formula I-a. Any conventional method for reduction of an amide can be utilized for this conversion. In accordance with the preferred embodiment of this invention, compounds of formula 21 are heated with borane-tetrahydrofuran complex at temperatures between about 50° C. and about 90° C. to afford compounds of formula I-a that can be converted to a pharmaceutically acceptable salt using any conventional method.

accordance with the preferred embodiment of this invention, compounds of formula 20 are treated with an alkyl halide using sodium hydride as base to afford compounds of formula 21. Compounds of formula 21 can be converted in two steps to compounds of formula I-aa in an identical manner as previously described for the conversion of compounds of formula 20 to compounds of formula I-a (Scheme I). Compounds of formula I-a can be converted into a pharmaceutically acceptable salt using any conventional method.

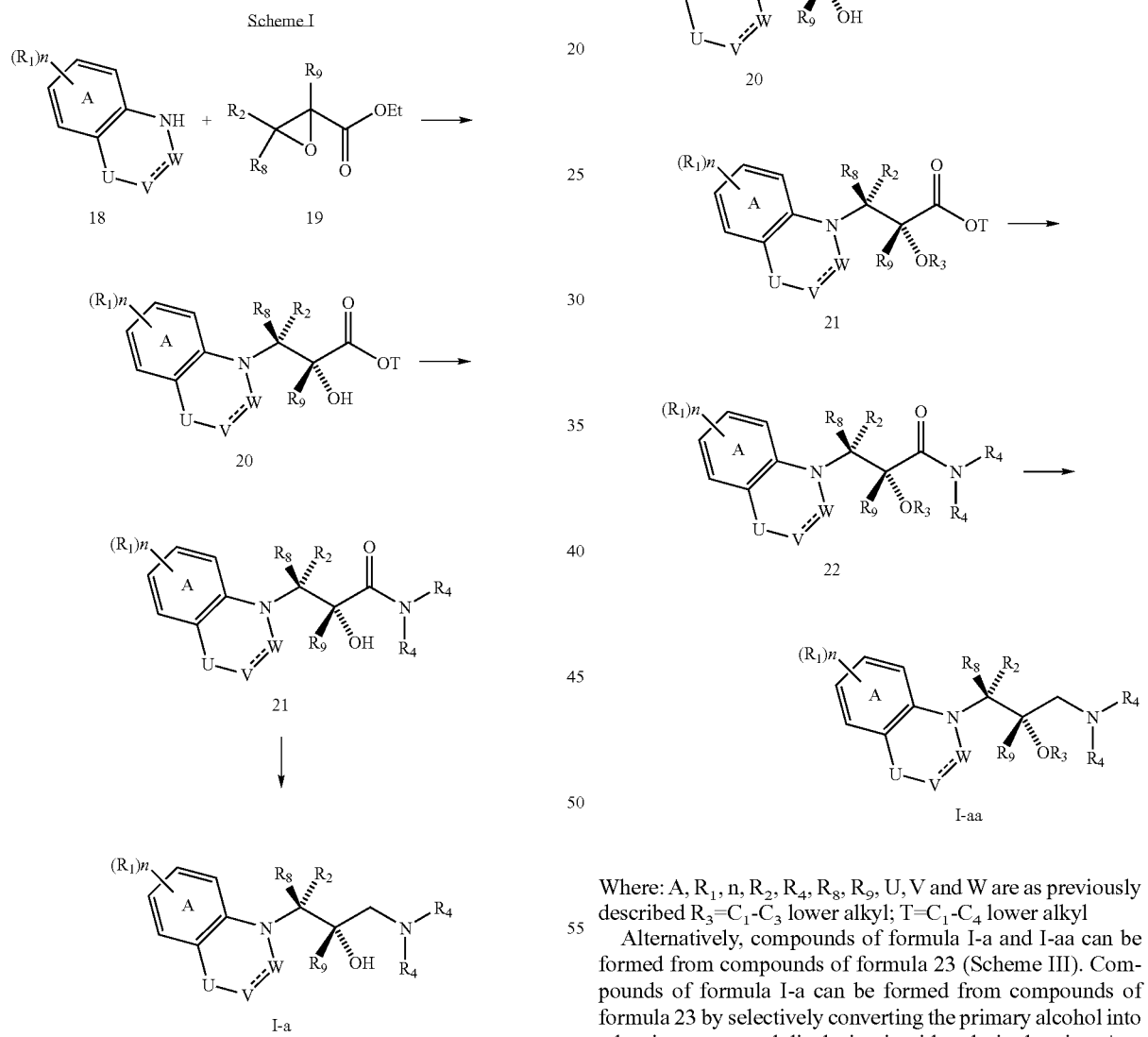

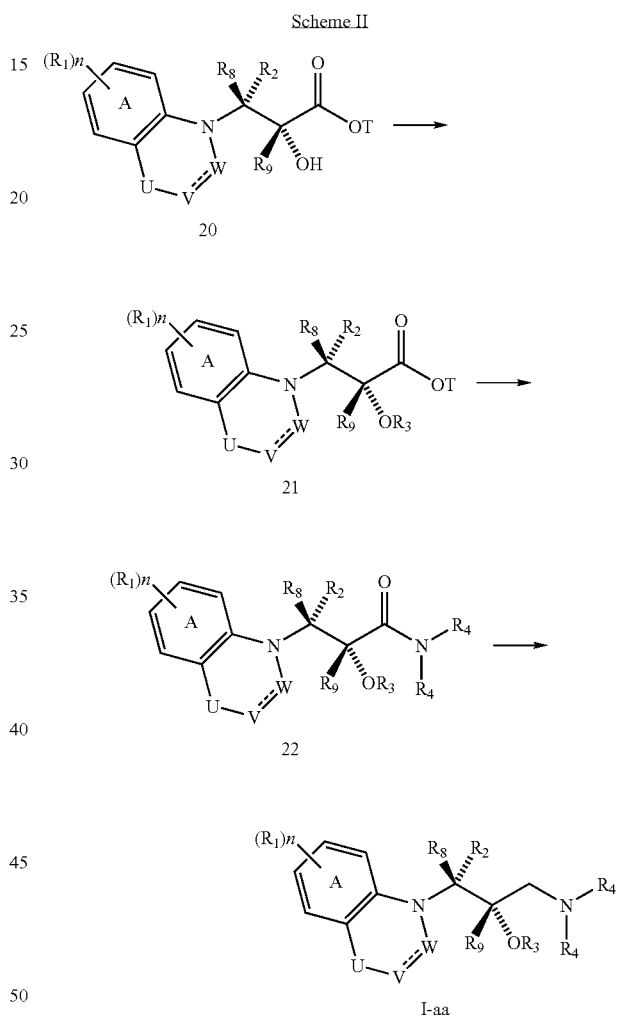

Where: A, $R_1$, n, $R_2$, $R_4$, $R_8$, $R_9$, U, V and W are as previously described. $T=C_1-C_4$ lower alkyl If it is desired to produce compounds of formula I-aa, they can be prepared via alkylation of compounds of formula 20 (Scheme III). Any conventional method for the alkylation of secondary alcohols can be employed for this conversion. In Where: A, $R_1$, n, $R_2$, $R_4$, $R_8$, $R_9$, U, V and W are as previously described $R_3=C_1-C_3$ lower alkyl; $T=C_1-C_4$ lower alkyl Alternatively, compounds of formula I-a and I-aa can be formed from compounds of formula 23 (Scheme III). Compounds of formula I-a can be formed from compounds of formula 23 by selectively converting the primary alcohol into a leaving group and displacing it with a desired amine. Any conventional method for the selective conversion of a primary alcohol into a leaving group and displacing it with an amine can be utilized for this conversion. In accordance with the preferred embodiment of this invention, the diol of formula 23 is treated with para-toluenesulfonyl chloride in pyridine to form the tosylate of formula 24, which is converted to the compound of formula I-a via treatment with an excess of an alcoholic amine solution, either at room temperature or heated to about 40° C. to about 80° C. in a sealed tube. Compounds of formula I-a can be converted to a pharmaceutically acceptable salt using any conventional method.

If it is desired to form compounds of formula I-aa, they can be prepared from compounds of formula 24 via alkylation followed by amination. Any conventional method of alkylating a hydroxyl group in the presence of a tosyl group can be employed for this conversion. In accordance with the preferred embodiment of this invention, compounds of formula 24 are treated with an alkyl trifluoromethanesulfonate, e.g. methyl trifluoromethanesulfonate, in the presence of a hindered base, e.g. 2,6-di-tert-butyl-4-methylpyridine. The reaction can be performed either at room temperature or heated to about 40° C. to about 80° C. Compounds of formula 25 can be converted to compounds of formula I-aa as previously described for the synthesis of compounds of formula I-a. Compounds of formula I-aa can be converted to a pharmaceutically acceptable salt using any conventional method.

hol into a leaving group can be utilized for this conversion. In accordance with the preferred embodiment of this invention, compounds of formula 23 are treated with para-nitrobenzoyl chloride in pyridine at low temperature (preferably below about 0° C.) to form compounds of formula 26. Compounds of formula 26 can be converted to a secondary mesylate of formula 27 via reaction with methanesulfonyl chloride in dichloromethane using triethylamine as base. The reaction is preferably carried out at temperatures between about −15° C. and about 10° C. Deprotection of the primary alcohol in compounds of formula 27 allows for the formation of a primary epoxide through an $S_N2$ reaction resulting in an inversion of the stereocenter. Any conventional method for deprotection of a primary alcohol, and any conventional method for epoxide formation onto an alpha leaving group can be employed for this conversion. In accordance with the preferred embodiment of this invention, compounds of formula 27 are treated with an aqueous solution of a suitable base in organic solvent, preferably, aqueous sodium hydroxide in

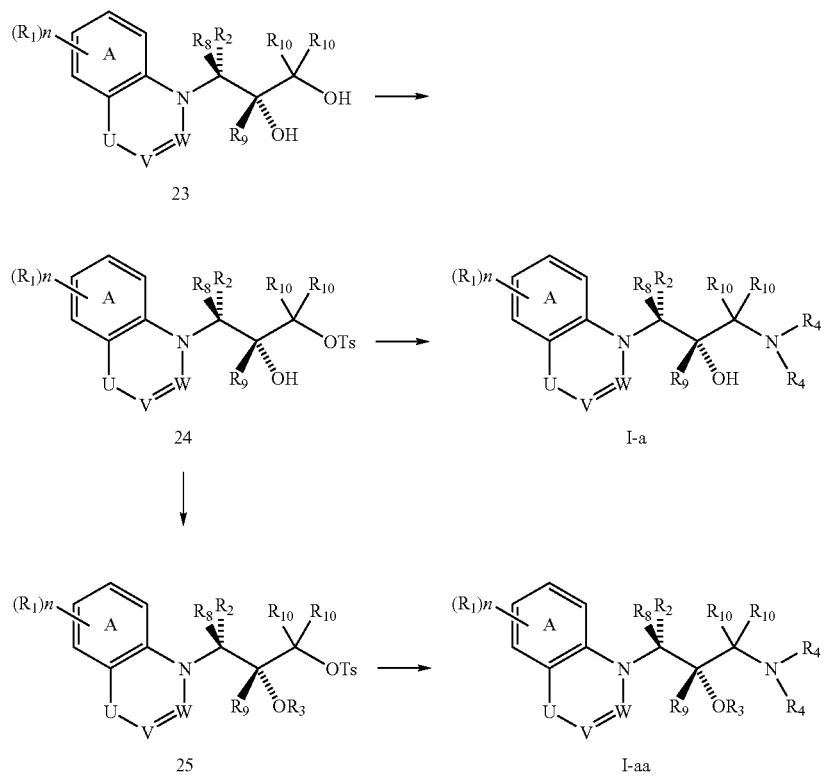

Scheme III

Where: A, $R_1$, n, $R_2$, $R_4$, $R_8$, $R_9$, $R_{10}$, U, V and W are as previously described $R_3=C_1-C_3$ lower alkyl; OTs=para-toluenesulfonylate or any conventional leaving group If it is desired to form compounds of formula I-b, they can be formed from compounds of formula 23 (Scheme IV). Compounds of formula 23 can be converted in four steps to compounds of formula I-b. This route involves the selective protection of the primary alcohol followed by conversion of the secondary alcohol to a leaving group. Any conventional method for the selective protection of a primary alcohol, and any conventional method for converting of a secondary alcodioxane. The resulting epoxide of formula 28 can be ring-opened regioselectively with an amine to produce the desired aminoalcohol of formula I-b. Any conventional method for the regioselective ring opening of a primary epoxide can be employed for this conversion. In accordance with the preferred embodiment of this invention, compounds of formula 28 are treated with an excess of an alcoholic amine solution in a sealed flask, either at room temperature or heated to about 40° C. to about 90° C. Compounds of formula I-b can be converted to a pharmaceutically acceptable salt using any conventional method.

Scheme IV

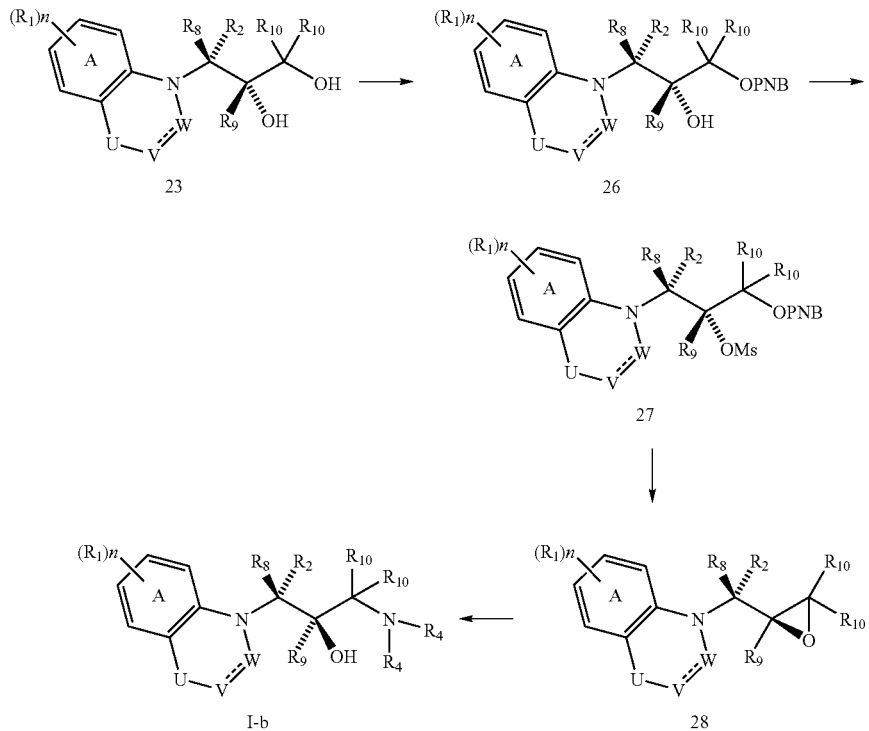

Where: A, $R_1$, n, $R_2$, $R_4$, $R_8$, $R_{10}$, U, V and W are as previously described $R_9$ is H PNB=para-nitrobenzoyl or any conventional protecting group; OMs=methanesulfonate or any conventional leaving group; T=$C_1$-$C_4$ lower alkyl If it is desired to form compounds of formula I-bb, they can be formed from compounds of formula I-b in three steps (Scheme V) in an identical manner as previously described for the conversion of compounds of formula I-b to compounds of formula I-bb (Scheme III). Compounds of formula I-bb can be converted to a pharmaceutically acceptable salt using any conventional method.

Scheme V

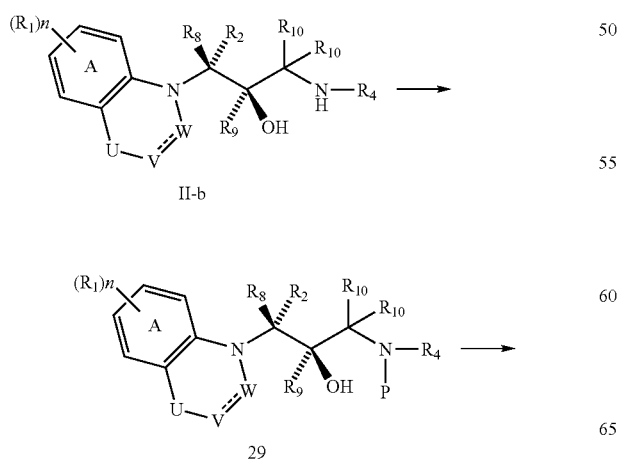

-continued

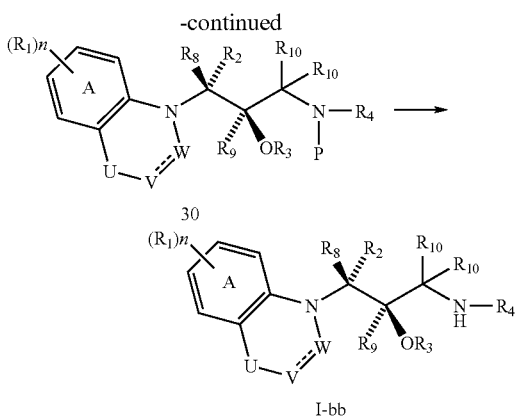

Where: A, $R_1$, n, $R_2$, $R_4$, $R_8$, $R_9$, $R_{10}$, U, V and W are as previously described $R_3$=$C_1$-$C_3$ lower alkyl, P=protecting group, preferably tert-butoxycarbonyl Compounds of formula 23 are formed via regio- and stereo-selective ring opening of an appropriately substituted epoxide of formula 17 (formed via an epoxidation of an appropriately substituted allylic alcohol) with an appropriately substituted compound of formula 18 (Scheme VI). Any conventional method for regio- and stereo-selective ring opening of an epoxide can be employed for this conversion. In accordance with the preferred embodiment of this invention, compounds of formula 18 are treated with a base, e.g. sodium hydride, sodium tert-butoxide, potassium hydroxide, potassium tert-butoxide or potassium hydroxide, then treated with the epoxide of formula 17. The epoxide of formula 17 can be pre-treated with a Lewis acid, e.g. titanium iso-propoxide, boron-trifluoride, etc. to ensure regio-selective ring-opening. The reaction occurs at room temperature over a duration of about 2 to about 72 hours. Alternatively, compounds of formula 18 that are suitably nucleophilic can be heated with the epoxide of formula 17 at temperatures from about 50° C. to about 170° C. to form compounds of formula 23.

Epoxidation of trans-allylic alcohols can be performed either racemically or asymmetrically using methods described in the literature. In accordance with the preferred embodiment of this invention, racemic epoxidation is conducted with either peracetic acid or meta-chloroperbenzoic acid. If it is desired to produce a single enantiomer of compounds of formula I, asymmetric epoxidation of an allylic alcohol can be performed with tert-butylhydroperoxide or cumene hydroperoxide in the presence of the appropriate tartrate ester, titanium (IV) isopropoxide, and molecular sieves. This method is well established in the literature (e.g. K. B. Sharpless, et. al., *J. Org. Chem.* 1986, 51, 3710). Compounds of formula 18 and the starting allylic alcohols are either available from commercial sources or are accessible through methods well established in the literature.

embodiment of this invention, racemic epoxidation of the trans-allylic ester is conducted using di-(trifluoromethyl)dioxirane formed in-situ from trifluoroacetone and oxone (Yang, D.; Wong, M.-K.; Yip *J. Org. Chem.* 1995, 60, 3887-3889). If it is desired to produce a single enantiomer of compounds of formula I, asymmetric epoxidation of an allylic ester can be performed with oxone and a chiral ketone as reported in the literature (W-Y. Wu, X. She, Y. Shi, *J. Am. Chem. Soc.* 2002, 124, 8792). Alternatively, compounds of formula 19 can be formed via the oxidation and esterification of compounds of formula 17 (described in Scheme VI). Any conventional method for the oxidation of an epoxy alcohol and any conventional method for the esterification of an epoxy acid can be utilized for this conversion. In accordance with the preferred embodiment of this invention, epoxy alcohol 17 is oxidized with sodium periodate and catalytic ruthenium trichloride in carbon tetrachloride, buffered with sodium bicarbonate. The resulting acid can be esterified with diazomethane or with catalytic sulfuric acid in ethanol to form compounds of formula 19.

Scheme VII

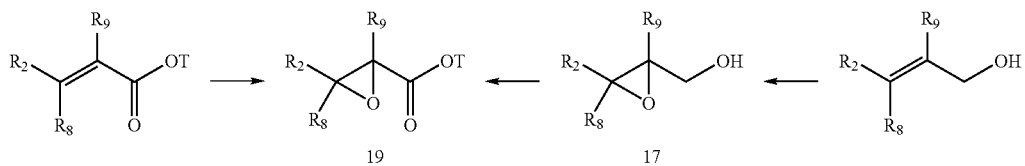

Where: $R_2$, $R_8$ and $R_9$ are as previously described

And where: $T = C_1-C_4$ lower alkyl

In other embodiments, the invention is directed to pharmaceutical compositions, comprising:

a. at least compound of formula I, or pharmaceutically acceptable salt thereof; and b. at least one pharmaceutically acceptable carrier.

Generally, the compound of formula I, or a pharmaceutically acceptable salt thereof, will be present at a level of from about 0.1%, by weight, to about 90% by weight, based on the total weight of the pharmaceutical composition, based on the total weight of the pharmaceutical composition. Preferably, the compound of formula I, or a pharmaceutically acceptable salt thereof, will be present at a level of at least about 1%, by weight, based on the total weight of the pharmaceutical composition. More preferably, the compound of formula I, or a pharmaceutically acceptable salt thereof, will be present at a level of at least about 5%, by weight, based on the total weight of the pharmaceutical composition. Even more preferably, the norepinephrine reuptake inhibitor or a pharmaceutically acceptable salt thereof will be present at a level of at least about 10%, by weight, based on the total weight of the pharmaceutical composition. Yet even more preferably, the compound of formula I, or a pharmaceutically acceptable salt thereof, will be present at a level of at least about 25%, by weight, based on the total weight of the pharmaceutical composition.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers are those Scheme VI

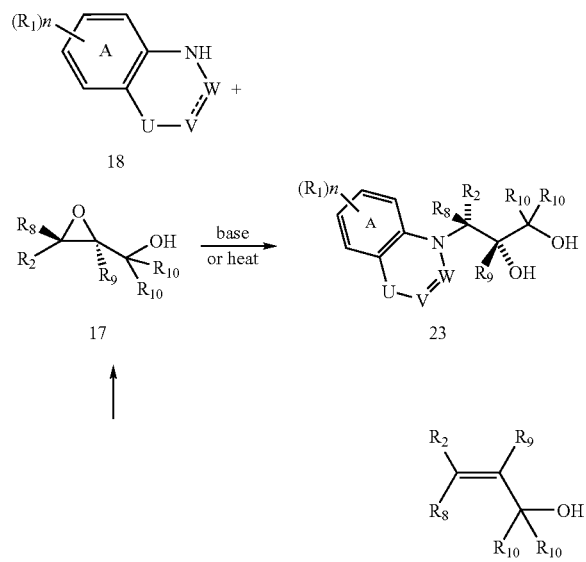

Where: A, $R_1$, n, $R_2$, $R_8$, $R_9$, $R_{10}$, U, V and W are as previously described Compounds of formula 19 can be formed either racemically or asymmetrically using methods described in the literature starting with either trans-allylic esters or trans-allylic alcohols (Scheme VII). In accordance with the preferred that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes use of each type of therapeutic agent in a concurrent manner. In either case, the treatment regimen will provide beneficial effects of the drug combination in treating the conditions or disorders described herein.

The route of administration may be any route, which effectively transports the active compound of formula I, or a pharmaceutically acceptable salt thereof, to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of compound of formula I, or pharmaceutically acceptable salt thereof, with other active ingredients may be concurrent or simultaneous.

It is believed that the present invention described presents a substantial breakthrough in the field of treatment, alleviation, inhibition, and/or prevention of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

Accordingly, in one embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

"Vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject.

The term "sexual dysfunction" includes, but is not limited to, condition relating to desire and/or arousal.

As used herein, "gastrointestinal and genitourinary disorders" includes irritable bowel syndrome, symptomatic GERD, hypersensitive esophagus, nonulcer dyspepsia, non-cardiac chest pain, biliary dyskinesia, sphincter of Oddi dysfunction, incontinence (i.e., urge incontinence, stress incontinence, genuine stress incontinence, and mixed incontinence) (including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, "nervous system disorders," includes addictive disorders (including those due to alcohol, nicotine, and other psychoactive substances) and withdrawal syndrome, age-associated learning and mental disorders (including Alzheimer's disease), anorexia nervosa, bulimia nervosa, attention-deficit disorder with or without hyperactivity disorder bipolar disorder, pain, cyclothymic disorder, depression disorder (including major depressive disorder, refractory depression adolescent depression and minor depression), dysthymic disorder, generalized anxiety disorder (GAD), obesity (i.e., reducing the weight of obese or overweight patients), obsessive compulsive disorders and related spectrum disorders, oppositional defiant disorder, panic disorder, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), selective serotonin reuptake inhibition (SSRI) "poop out" syndrome (i.e., wherein a patient who fails to maintain a satisfactory response to SSRI therapy after an initial period of satisfactory response).

As used herein, "pain," includes both acute pain and chronic pain, which may be centralized pain, peripheral pain, or combination thereof. The term includes many different types of pains including, but not limited to, neuropathic pain, visceral pain, musculoskeletal pain, bony pain, cancer pain, inflammatory pain, and combinations thereof, such as lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, neuropathic pain such as peripheral neuropathy and diabetic neuropathy, post-operative pain, and pain which is co-morbid with nervous system disorders described herein.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring), including, for the purpose of the present invention, neuropathic pain and cancer pain. Chronic pain includes neuropathic pain, hyperalgesia, and/or allodynia.

As used herein, the term "neuropathic pain" refers to chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or exhibitory functions and abnormal interactions between the parasympathetic and sympathetic nervous systems. A wide range of clinical conditions may be associated with or form the basis for neuropathic pain including, for example, diabetes, post traumatic pain of amputation (nerve damage cause by injury resulting in peripheral and/or central sensitization such as phantom limb pain), lower back pain, cancer, chemical injury, toxins, other major surgeries, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, or viral or bacterial infections such as shingles or human immunodeficiency virus (HIV), and combinations thereof. Also included in the definition of neuropathic pain is a condition secondary to metastatic infiltration, adiposis dolorosa, burns, central pain conditions related to thalamic conditions, and combinations thereof.

As used herein, the term "hyperalgesia" refers to pain where there is an increase in sensitivity to a typically noxious stimulus.

As used herein, the term "allodynia" refers to an increase in sensitivity to a typically non-noxious stimulus.

As used herein, the term "visceral pain" refers to pain associated with or resulting from maladies of the internal organs, such as, for example, ulcerative colitis, irritable bowel syndrome, irritable bladder, Crohn's disease, rheumatologic (arthralgias), tumors, gastritis, pancreatitis, infections of the organs, biliary tract disorders, and combinations thereof.

As used herein, the term "female-specific pain" refers to pain that may be acute and/or chronic pain associated with female conditions. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes, and combinations thereof.

In one embodiment, the present invention is directed to methods for treating or preventing vasomotor symptoms in a subject in need thereof, comprising the step of:

administering to said subject an effective amount of at least one compound of formula I or pharmaceutically acceptable salt thereof.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
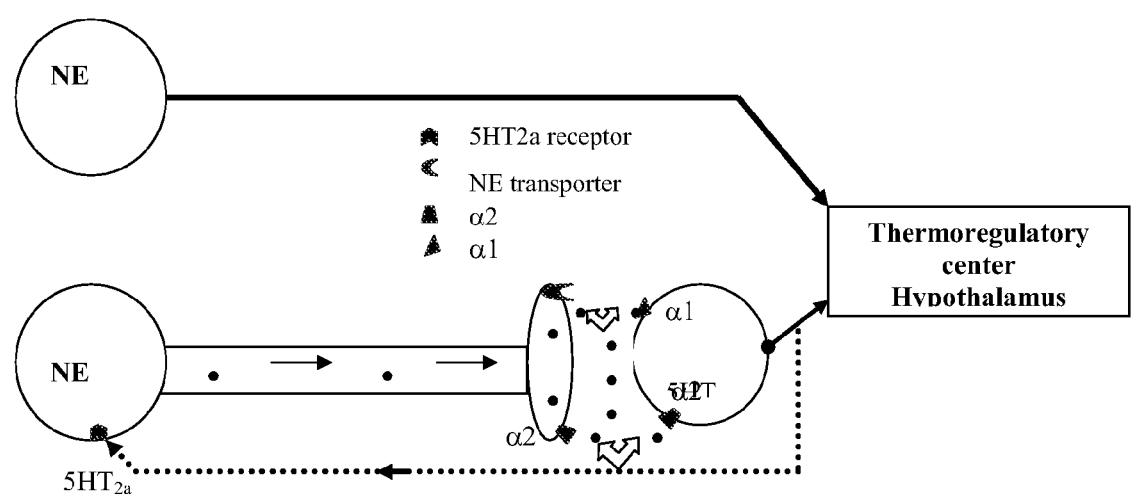
FIG. 2 is a schematic representation of the interactions of norepinephrine and serotonin and their respective receptors (5-HT$_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha 1}$ and adrenergic$_{\alpha 2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibit the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic$_{\alpha 2}$ receptor with an antagonist, or (iii) blocking the activity of 5-HT on NE neurons with a 5-HT$_{2a}$ antagonist.

In another embodiment, the present invention is directed to methods for treating or preventing a depression disorder in a subject in need thereof, comprising the step of:

administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:

administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromyalgia syndrome in a subject in need thereof, comprising the step of:

administering to said subject an effective amount of a compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

(1RS,2SR)-1-(1H-indol-1-yl)-3-(4-methylpiperazin-1-yl)-1-phenyl propan-2-ol dihydrochloride

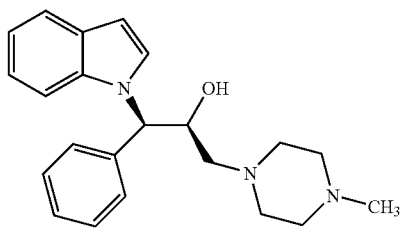

Step 1: A mixture of indole (2.34 g, 20 mmol) and pulverized solid potassium hydroxide (1.12 g, 20 mmol) was stirred for 30 minutes under nitrogen at room temperature. Trans-3-phenylglycidol (3.0 g, 20 mmol) in dimethylsulfoxide (1 mL) was then added and the mixture was stirred at 70° C. for 2 hours until no epoxide remained. The mixture was then cooled and partitioned between water and dichloromethane. The organic layer was separated, washed with water several times, dried over anhydrous sodium sulfate, filtered, and concentrated in vacuo. The crude product was purified via Biotage chromatography (FlasH40i, silica, 10%, 20%, 30% ethyl acetate/hexane) to yield 1.92 g (36%) of (2RS,3RS)-3-indol-1-yl-3-phenyl-propane-1,2-diol as an oil. $^1$HNMR (DMSO): δ3.27 (m, 2H, CH$_2$OH), δ4.45 (m, 1H, CHOH), δ4.80 (t, 1H, CH$_2$OH), δ5.20 (d, 1H, CHOH), δ5.60 (d, 1H, CHPh); MS (ESI) m/z 268 ([M+H]$^+$).

Step 2: A solution of (2RS,3RS)-3-indol-1-yl-3-phenyl-propane-1,2-diol (1.83 g, 6.8 mmol) and p-toluenesulfonyl chloride (1.31 g, 6.8 mmol) in anhydrous pyridine (10 mL) was stirred at room temperature under nitrogen for 15 hours. The mixture was then diluted with water (10 mL), quenched with a 2N aqueous solution of hydrochloric acid in an ice/water bath until the solution was pH=3, and extracted with dichloromethane. The organic layer was washed with water again, dried over anhydrous sodium sulfate, filtered, and concentrated. The residue was purified via Biotage chromatography (FlasH40i, silica, 10%, 25% EtOAc/hexane) to yield 1.98 g (69%) of (2RS,3RS)-toluene-4-sulfonic acid 2-hydroxy-3-indol-1-yl-3-phenyl-propyl ester as a white solid. $^1$HNMR (DMSO): δ3.70 and δ3.85 (dd and dd, 2H, CH$_2$OTs), δ4.80 (m, 1H, CHOH), δ5.52 (d, 1H, CHPh), δ5.82 (d, 1H, CHOH); MS (ESI) m/z 422 ([M+H]$^+$).

Step 3: A mixture of (2RS,3RS)-toluene-4-sulfonic acid 2-hydroxy-3-indol-1-yl-3-phenyl-propyl ester (0.185 g, 0.4 mmol), 1-methyl piperazine (0.05 mL, 0.4 mmol) and potassium carbonate (0.07 g, 0.44 mmol) in acetonitrile (10 mL) was stirred at reflux under nitrogen for 24 hours. After cooling, the mixture was filtered and the filtrate was concentrated and purified via Biotage chromatography (5% methanol/dichloromethane) to give a white solid of (1RS,2SR)-1-(1H-indol-1-yl)-3-(4-methylpiperazin-1-yl)-1-phenylpropan-2-ol. The free base was dissolved in a minimum amount of ethanol and treated with a 1N ethereal solution of hydrochloric acid until the solution was pH=3 followed by diethyl ether. The product was then crystallized by adding a minimum amount of hexane to afford the titled compound, (1RS,2SR)-1-(1H-indol-1-yl)-3-(4-methylpiperazin-1-yl)-1-phenylpropan-2-ol dihydrochloride as an off-white solid. MS m/z 350 ([M+H]$^+$); HRMS: calcd for $C_{22}H_{27}N_{3O}$+H+, 350.22269; found (ESI, [M+H]+), 350.2228.

Example 2

(1RS,2SR)-1-(2,3-dihydro-4H-1,4-benzoxazin-4-yl)-3-(methylamino)-1-phenylpropan-2-ol dihydrochloride

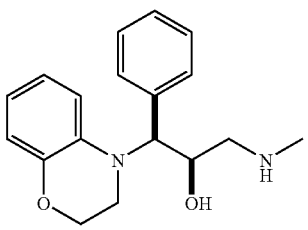

A mixture of 3,4-dihydro-2H-benzo[1,4]oxazine (2.027 g 15.00 mmol) and trans-ethyl-3-phenylglycidate (2.883 g, 15.00 mmol) was stirred at 135° C. for 12 hours. After cooling, the viscous liquid was purified via Biotage Horizon (FLASH 40 M, silica, 10%, 20%, 30% EtOAc/hexane) and recrystallized (minimal warm chloroform/hexane/−20° C.) to yield 4.261 g (87%) ethyl (2RS,3RS)-3-(2,3-dihydro-4H-1, 4-benzoxazin-4-yl)-2-hydroxy-3-phenylpropanoate as a white solid. MS (ESI) m/z 328.0 ([M+H]$^+$).

A mixture of ethyl (2RS,3RS)-3-(2,3-dihydro-4H-1,4-benzoxazin-4-yl)-2-hydroxy-3-phenylpropanoate (283 mg, 0.864 mmol) and ethanolic methylamine solution (5 mL, 33% in ethanol) was stirred at 70° C. in a sealed tube for 5 hours. After cooling, all volatiles were removed under reduced pressure. The resulting yellow solid was purified via Biotage Horizon (FLASH 12 S, silica, 20%, 35%, 50% EtOAc/hexane) to yield 235 mg (87%) (2RS,3RS)-3-(2,3-dihydro-4H-1,4-benzoxazin-4-yl)-2-hydroxy-N-methyl-3 phenylpropanamide as a white solid. MS (ESI) m/z 311.0 ([M−H]$^-$).

A solution of (2RS,3RS)-3-(2,3-dihydro-4H-1,4-benzoxazin-4-yl)-2-hydroxy-N-methyl-3 phenylpropanamide (216 mg, 0.692 mmol) in dry tetrahydrofuran (3 mL) under nitrogen was treated dropwise with a solution of borane (1.0 M in tetrahydrofuran, 3.50 mL, 3.50 mmol), and the resulting solution was stirred at 70° C. for 2 hours. After cooling in an ice bath, the reaction mixture was treated with a 2N aqueous solution of hydrochloric acid (1 mL), and the resulting mixture was heated at 50° C. for 30 minutes. Tetrahydrofuran was removed under reduced pressure, and the aqueous residue was dissolved in water (5 mL) and washed with diethyl ether (10 mL). The aqueous layer was made alkaline with solid potassium carbonate and extracted with ethyl acetate (2×10 mL). The combined organic extracts were washed with brine, dried (sodium sulfate) and concentrated under reduced pressure to yield 202 mg (98%) (1RS,2SR)-1-(2,3-dihydro-4H-1,4-benzoxazin-4-yl)-3-(methylamino)-1-phenylpropan-2-ol as a colorless oil. This oil was dissolved in ethanol (1 mL) and treated with a solution of hydrochloric acid (0.5 mL, 4M in 1,4-dioxane). All volatiles were again removed under reduced pressure. The resulting white solid was recrystallized (minimal warm ethanol/ethyl ether/−20° C.) to yield 105 mg (41%) (1RS,2SR)-1-(2,3-dihydro-4H-1,4-benzoxazin-4-yl)-3-(methylamino)-1-phenylpropan-2-ol dihydrochloride as a white solid. MS (ESI) m/z 299.0 ([M+H]$^+$);

HRMS: calcd for $C_{18}H_{22}N_2O_2$+H+, 299.17540; found (ESI, [M+H]$^+$), 299.1755.

Example 3

(1S,2R)-1-(3-chlorophenyl)-1-(1H-indol-1-yl)-3-(methylamino)propan-2-ol hydrochloride

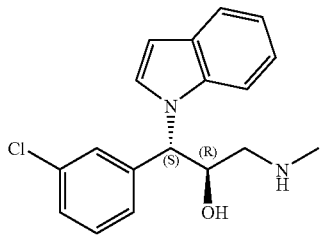

Step 1: A suspension of sodium hydride (60% in mineral oil, 4.0 g, 100 mmol) in tetrahydrofuran (600 mL) was treated dropwise with diethyl ethoxycarbonylmethylphosphonate (20 mL, 100 mmol) at 23° C. After 1 hour s,3-chlorobenzaldehyde (9.3 mL, 82 mmol) was added. After an additional 1 hour, the reaction was quenched with water (20 mL) and concentrated under vacuum to remove tetrahydrofuran. The residue was taken up in ethyl acetate (300 mL), washed with water (5×300 mL) and brine (1×300 mL), dried (magnesium sulfate) and concentrated under vacuum to provide (2E)-3-(3-chlorophenyl)-acrylic acid ethyl ester (18 g, quantitative) as a clear, pale yellow oil. MS (ESI) m/z 210 ([M+H]$^+$).

Step 2: (2E)-3-(3-Chlorophenyl)-acrylic acid ethyl ester (17.6 g, 82 mmol) was dissolved in dry dichloromethane (300 mL), cooled to −78° C. and treated with a solution of di-iso-butylaluminum hydride (1.0 M solution in hexane, 250 mL, 250 mmol) over 20 minutes. After 1.5 hours total, the reaction was quenched with methanol (75 mL) at −78° C., warmed to 23° C. and treated with a saturated aqueous solution of potassium sodium tartrate (300 mL). The aqueous phase was separated and extracted with dichloromethane (2×300 mL). The combined extracts were washed with a saturated aqueous solution of sodium tartrate (450 mL), dried (sodium sulfate) and concentrated under vacuum to provide a cloudy yellow oil (14.6 g) that was pre-adsorbed on silica gel (25 g). Flash column chromatography (silica 250 g, 10%, 20% ethyl acetate/hexanes) provided (2E)-3-(3-chlorophenyl)prop-2-en-1-ol (12.4 g, 90%) as a clear, colorless oil. MS (ESI) m/z 151 ([M+H−H$_2$O]$^+$).

Step 3: In an analogous manner to EXAMPLE 10, step 4, [(2R,3R)-3-(3-chlorophenyl)oxiran-2-yl]methanol was prepared from (2E)-3-(3-chlorophenyl)prop-2-en-1-ol. MS (ESI) m/z 167 ([M+H−H$_2$O]$^+$).

Step 4 (Method A): In an analogous manner to EXAMPLE 10, step 5, (2S,3S)-3-(3-chlorophenyl)-3-(1H-indol-1-yl)propane-1,2-diol was prepared from 1H-indole and [(2R,3R)-3-(3-chlorophenyl)oxiran-2-yl]methanol. MS (ES) m/z 302 ([M+H]$^+$).

Step 4a (Method B): [(2R,3R)-3-(3-chlorophenyl)oxiran-2-yl]methanol (4.8 g, 26 mmol) and indoline (d 1.063, 2.9 mL, 26 mmol) were heated neat at 135° C. in a sealed flask. After 1.5 hours, the cooled mixture was pre-adsorbed on silica gel (25 g). Flash column chromatography (silica 375 g, 20%, 40%, 80% ethyl acetate/hexanes) provided (2S,3S)-3-(3-chlorophenyl)-3-(2,3-dihydro-1H-indol-1-yl)propane-1, 2-diol (5.8 g, 73%) as a white solid. MS (ES) m/z 304 ([M+H]$^+$).

Step 4b (Method B): A solution of (2S,3S)-3-(3-chlorophenyl)-3-(2,3-dihydro-1H-indol-1-yl)propane-1,2-diol (5.8 g, 19 mmol) in ca. 1:1 (v/v) toluene-dichloromethane (200 mL) was treated with a solution of 2,3-dichloro-5,6-dicyano-1,4-benzoquinone (4.4 g, 19 mmol) in toluene (100 mL) at 0° C. After 30 minutes, the mixture was diluted with ethyl acetate (1 L) and washed with 5% aqueous sodium carbonate (4×1 L), water (1 L) and brine (1 L), dried (magnesium sulfate) and concentrated under vacuum to give a dark oil (5.4 g) that was pre-adsorbed on silica gel (15 g). Flash column chromatography (silica 235 g, 20%, 40% ethyl acetate/hexanes) provided (2S,3S)-3-(3-chlorophenyl)-3-(1H-indol-1-yl)propane-1,2-diol, (4.7 g, 82%) as a cloudy yellow oil. MS (ES) m/z 302 ([M+H]$^+$).

Step 5: In an analogous manner to EXAMPLE 1, step 2, (2S,3S)-toluene-4-sulfonic acid 3-(3-chlorophenyl)-2-hydroxy-3-indol-1-yl-propyl ester was prepared from (2S,3S)-3-(3-chlorophenyl)-3-(1H-indol-1-yl)propane-1,2-diol. MS (ES) m/z 456 ([M+H]$^+$).

Step 6: (2S,3S)-Toluene-4-sulfonic acid 3-(3-chlorophenyl)-2-hydroxy-3-indol-1-yl-propyl ester (0.60 g, 1.2 mmol)

was treated with a solution of methylamine in methanol (2.0 M, 3 mL, 6 mmol) and the solution was stirred at 23° C. for 18 hours. At this time, the solution was concentrated under vacuum and dissolved in diethyl ether (50 mL). The organic solution was washed with a 1 N aqueous solution of sodium hydroxide (50 mL), water (50 mL) and brine (50 mL), dried (sodium sulfate) and concentrated under vacuum to provide an orange foam (0.30 g) that was purified by reverse phase HPLC (90:10 water-acetonitrile to 50:50 water-acetonitrile containing 0.1% trifluoroacetic acid @ 20 mL/min). The product fractions were concentrated under vacuum to remove acetonitrile and the aqueous solution was basified with a 2N aqueous solution of ammonium hydroxide. The resulting milky suspension was extracted with ethyl acetate (200 mL) and the organic phase was washed with water (200 mL) and brine (100 mL), dried (sodium sulfate) and concentrated under vacuum. The residue was dissolved in absolute ethanol (4 mL), treated with a 4 M hydrochloric acid in 1,4-dioxane (1.3 eq) and stirred for 10 minutes. The solution was concentrated under vacuum, then dissolved in absolute ethanol (3 mL) and left standing at 23° C. overnight. Vacuum filtration provided (1S,2R)-1-(3-chlorophenyl)-1-(1H-indol-1-yl)-3-(methylamino)propan-2-ol hydrochloride (62 mg, 5% for 3 steps) as a white crystalline solid. HRMS calcd for $C_{18}H_{19}ClN_2O+H^+$, 315.12587; found (ESI) 315.1267 ([M+H]$^+$).

Example 4

(1SR,2RS)-3-(methylamino)-1-(4-methyl-3,4-dihydroquinoxalin-1(2H)-yl)-1-phenylpropan-2-ol hydrochloride

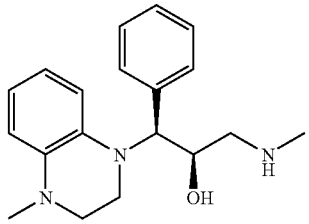

Step 1: In an analogous manner to EXAMPLE 7, step 3, 3-phenylglycidol was prepared from cinnamyl alcohol as a white solid. MS (ES) m/z 151.1 ([M+H]$^+$).

Step 2: In an analogous manner to EXAMPLE 6, step 4, (2SR,3SR)-3-(4-methyl-3,4-dihydroquinoxalin-1(2H)-yl)-3-phenylpropane-1,2-diol was prepared from 1-methyl-1,2,3,4-tetrahydroquinoxaline[1] and 3-phenylglycidol as a viscous colorless oil. MS (ES) m/z 299.0 ([M+H]$^+$); HRMS: calcd for $C_{18}H_{22}N_2O_2+H^+$, 299.1760; found (ESI, [M+H]$^+$), 299.1739.

[1] Cavagnol, J. C.; Wiselogle, F. Y. *J. Am. Chem. Soc.* 1947, 69, 795-799.

Step 3: In an analogous manner to EXAMPLE 6, step 6, (1SR,2RS)-3-(methylamino)-1-(4-methyl-3,4-dihydroquinoxalin-1(2H)-yl)-1-phenylpropan-2-ol hydrochloride was prepared from (2SR,3SR)-3-(4-methyl-3,4-dihydroquinoxalin-1(2H)-yl)-3-phenylpropane-1,2-diol as a white powder. MS (ES) m/z 312.0 ([M+H]$^+$); HRMS: calcd for $C_{19}H_{25}N_3O+H^+$, 312.2076; found (ESI, [M+H]$^+$), 312.2065.

Example 5

(1SR,2RS)-3-(methylamino)-1-phenyl-1-[4-(2,2,2-trifluoroethyl)-3,4-dihydroquinoxalin-1(2H)-yl]propan-2-ol hydrochloride

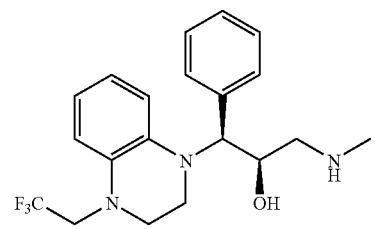

Compound 1-(2,2,2-trifluoroethyl)-1,2,3,4-tetrahydroquinoxaline was obtained as a white powder side product of the reduction reaction of quinoxaline to 1,2,3,4-tetrahydroquinoxaline using sodium borohydride in trifluoroacetic acid.[2] MS (ES) m/z 217.1 ([M+H]$^+$).

[2] Bugle, R. C.; Osteryoung, R. A. *J. Org. Chem.* 1979, 44, 1719-1720.

In an analogous manner to EXAMPLE 6, step 4, (2SR,3SR)-3-(4-(2,2,2-trifluoroethyl)-3,4-dihydroquinoxalin-1(2H)-yl)-3-phenylpropane-1,2-diol was prepared from 1-(2,2,2-trifluoroethyl)-1,2,3,4-tetrahydroquinoxaline and 3-phenylglycidol (EXAMPLE 4, step 1) as a viscous colorless oil.

In an analogous manner to EXAMPLE 6, step 6, (1SR,2RS)-3-(methylamino)-1-phenyl-1-[4-(2,2,2-trifluoroethyl)-3,4-dihydroquinoxalin-1(2H)-yl]propan-2-ol hydrochloride was prepared from (2SR,3SR)-3-(4-(2,2,2-trifluoroethyl)-3,4-dihydroquinoxalin-1(2H)-yl)-3-phenylpropane-1,2-diol as a white powder. MS (ES) m/z 380.0 ([M+H]$^+$); HRMS: calcd for $C_{20}H_{24}F_3N_3O+H^+$, 380.1950; found (ESI, [M+H]$^+$), 380.1934.

Example 6

(1S,2R)-1-(3-fluorophenyl)-1-(1H-indol-1-yl)-3-(methylamino)propan-2-ol hydrochloride

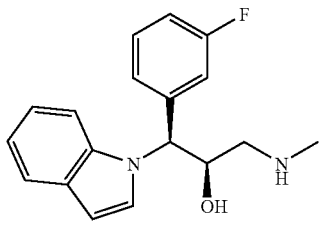

Step 1: To a mixture of trans-3-fluorocinnamic acid (50 g, 300 mmol) and iodomethane (300 mL) in acetone (1 L) was added portionwise cesium carbonate (147 g, 450 mmol, 1.5 equiv.), and the mixture was heated at 65° C. for 1.5 hours in a sealed reaction vessel. Upon cooling to room temperature, the reaction mixture was diluted with ethyl acetate (1 L), filtered through a pad of silica gel, and concentrated to give 47.33 g (87%) of trans-3-fluorocinnamic acid methyl ester as a colorless oil. MS (ES) m/z 180.0 (M$^+$).

Step 2: To a solution of trans-3-fluorocinnamic acid methyl ester (69.61 g, 386 mmol) in dry dichloromethane (1 L) at −78° C. under nitrogen was added dropwise diisobutylaluminum hydride (neat, 172 mL, 965 mmol, 2.5 equiv.) via an addition funnel. After the addition was complete, the reaction mixture was allowed to warm to −30° C. and stirred for an additional 1 hour, then quenched with methanol (150 mL). Upon warming to room temperature, the reaction mixture was treated with saturated aqueous solution of sodium/potassium tartrate (300 mL) and stirred for 30 minutes. The organic layer was washed sequentially with 1N aqueous hydrochloric acid solution, saturated aqueous sodium bicarbonate solution, brine, and dried (anhydrous sodium sulfate). The crude oil was purified by silica gel chromatography (0-50% ethyl acetate:hexane) to give 53.07 g (90%) of trans-3-fluorocinnamyl alcohol as a colorless oil. MS (ES) m/z 152.1 (M+).

Step 3: An oven-dried, 3-neck, 2-L round bottom flask fitted with two oven-dried addition funnels and a rubber septum was charged with diisopropyl D-tartrate (11.55 g, 49.3 mmol, 0.30 equiv.), 4 Å powdered, activated molecular sieves (40 g) and dry dichloromethane (800 mL) under nitrogen. After being cooled to −25° C., to the reaction mixture was added titanium isopropoxide (9.6 mL, 33 mmol, 0.20 equiv.) slowly via a hypodermic syringe. After stirring for 10 minutes, anhydrous t-butyl hydroperoxide (5.5 M in decane, 75.0 mL, 413 mmol, 2.5 equiv.) was added at a moderate rate via an addition funnel. The resulting mixture was stirred at −25° C. for 30 minutes. trans-3-Fluorocinnamyl alcohol (25.0 g, 164 mmol) in dry dichloromethane (50 mL) was added dropwise via an addition funnel while maintaining the temperature at −25° C. After the addition, the reaction mixture was stirred at −25° C. for 1 hour and at −20° C. for another 3 hours. After the reaction was complete, cooled aqueous sodium hydroxide solution (30%, 20 mL) saturated with sodium chloride was added slowly at −20° C. After diethyl ether (150 mL) was added, the cold bath was removed and the mixture was allowed to warm to ~5° C. and stirred for 1 hour. Magnesium sulfate (anhydrous, 50 g) was added and the mixture was stirred for 20 minutes, then filtered through a pad of silica gel, and washed with ether (300 mL). The filtrate was concentrated and toluene was used to azeotropically remove excess t-butyl hydroperoxide. The residual oil was purified on silica gel (0-30% ethyl acetate:hexane) to give 24.80 g (90%) of [(2R,3R)-3-(3-fluorophenyl)oxiran-2-yl]methanol as a viscous, colorless oil. Percent ee: >96.5%. MS (ESI) m/z 169.1 ([M+H]+).

Step 4: A mixture of indoline (1.42 g, 11.89 mmol) and [(2R,3R)-3-(3-fluorophenyl)oxiran-2-yl]methanol (2.0 g, 11.89 mmol) was heated at 125° C. for 5 hours in a sealed reaction vial. Upon cooling, the crude product was dissolved in ethyl acetate, absorbed on Fluorocil, and purified by Biotage chromatography (FlasH40i, silica, 0-55% EtOAc/hexane) to give 2.55 g (75%) of (2S,3S)-3-(2,3-dihydro-1H-indol-1-yl)-3-(3-fluorophenyl)propane-1,2-diol as a colorless oil. MS (ESI) m/z 288.1 ([M+H]+).

Step 5: A mixture of (2S,3S)-3-(2,3-dihydro-1H-indol-1-yl)-3-(3-fluorophenyl)propane-1,2-diol (2.00 g, 6.96 mmol) and activated manganese dioxide (20.0 g, 230 mmol) in dichloromethane (30 mL) was stirred at 20° C. for 3 hours. The mixture was diluted with ethyl acetate (15 mL), filtered through a pad of silica gel, and concentrated. The crude product was purified by Biotage chromatography (FlasH40i, silica, 0-70% EtOAc/hexane) to give 1.40 g (71%) of (2S,3S)-3-(3-fluorophenyl)-3-(1H-indol-1-yl)propane-1,2-diol as a colorless oil. MS (ESI) m/z 286.0 ([M+H]+). HRMS: calcd for $C_{17}H_{16}FNO_2$+H+, 286.1238; found (ESI, [M+H]+), 286.1239.

Step 6: To a solution of (2S,3S)-3-(2,3-dihydro-1H-indol-1-yl)-3-(3-fluorophenyl)propane-1,2-diol (452 mg, 1.586 mmol) in dichloromethane (3 mL) under nitrogen was added triethylamine (1.1 mL, 7.93 mmol). The mixture was cooled to 0° C., and para-toluenesulfonyl chloride (423 mg, 2.22 mmol) was added portionwise. The reaction mixture was stirred at 0° C. for 1 hour and stored at 0° C. overnight. Methylamine in absolute ethanol (8 M, 5 mL, 40 mmol) was added and the reaction mixture was sealed, and stirred overnight while warming to room temperature. All volatiles were removed under reduced pressure. The oil residue was dissolved in dichloromethane (20 mL), washed with aqueous potassium carbonate (5 mL), dried (anhydrous sodium sulfate), and concentrated. Purification by Biotage chromatography (FlasH12i, silica, 0-15% MeOH/dichloromethane/ 0.5% triethylamine) gave (1S,2R)-1-(3-fluorophenyl)-1-(1H-indol-1-yl)-3-(methylamino)propan-2-ol, which was dissolved dichloromethane (5 mL) and treated with a 1M ethereal solution of hydrochloric acid (1.9 mL, 1.9 mmol). To the resulting solution was added hexane until white powder formed, which was collected, washed with hexane, and dried in vacuo to yield 209 mg (44%) of (1S,2R)-1-(3-fluorophenyl)-1-(1H-indol-1-yl)-3-(methylamino)propan-2-ol hydrochloride as a white powder. MS (ES) m/z 299.0 ([M+H]+); HRMS: calcd for $C_{18}H_{19}FN_2O$+H+, 299.1554; found (ESI, [M+H]+), 299.1553.

Example 7

(1S,2R)-1-(1H-indol-1-yl)-3-(methylamino)-1-(2-methylphenyl)propan-2-ol hydrochloride

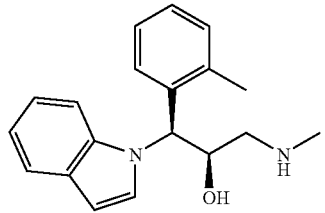

Step 1: In an analogous manner to EXAMPLE 6, step 1, trans-2-methylcinnamic acid methyl ester was prepared from trans-2-methylcinnamic acid.

Step 2: In an analogous manner to EXAMPLE 6, step 2, trans-2-methylcinnamyl alcohol was prepared from trans-2-methylcinnamic acid methyl ester as a colorless oil. MS (ES) m/z 146.9 ([M−H]−).

Step 3: To a solution of trans-2-methylcinnamyl alcohol (1.50 g, 10.14 mmol) in dichloromethane (30 mL) was added sodium carbonate (1.50 g, 14.19 mmol). The mixture was cooled to 10° C. and peracetic acid (32 wt %, 2.56 mL, 12.16 mmol) was added dropwise via an addition funnel. The reaction mixture was stirred for 3 hours while warming to room temperature, and quenched with saturated aqueous sodium sulfite solution (15 mL) slowly. More dichloromethane (30 mL) was added and the mixture was extracted. The organic layer was washed with brine, dried (anhydrous sodium sulfate), and concentrated. The oil residue was purified by silica gel chromatography (10-30% EtOAc/hexane) to give 920 mg (55%) of 3-(2-methylphenyl)glycidol as a colorless oil. HRMS: calcd for $C_{10}H_{12}O_2$+H+, 165.0916; found (ESI, [M+H]+), 165.0936.

Step 4: In an analogous manner to EXAMPLE 10, step 5, (2SR,3SR)-3-(1H-indol-1-yl)-3-(2-methylphenyl)propane- 1,2-diol was prepared from indole and 3-(2-methylphenyl) glycidol as a viscous, colorless liquid. MS (ES) m/z 282.2 ([M+H]$^+$);

HRMS: calcd for $C_{18}H_{19}NO_2$+H$^+$, 282.1494; found (ESI, [M+H]$^+$), 282.1499.

Step 5: In an analogous manner to EXAMPLE 6, step 6, (1SR,2RS)-1-(1H-indol-1-yl)-3-(methylamino)-1-(2-methylphenyl)propan-2-ol was prepared from (2SR,3SR)-3-(1H-indol-1-yl)-3-(2-methylphenyl)propane-1,2-diol as an oil.

Step 6: Racemic (1SR,2RS)1-(1H-indol-1-yl)-3-(methylamino)-1-(2-methylphenyl)propan-2-ol was dissolved in ethanol (20 mg/mL). The resulting solution was stack injected onto the Supercritical Fluid Chromatography instrument at 1 mL increments. The baseline resolved enantiomers, using the conditions described below, were collected. The enantiomeric purity of each enantiomer was determined under similar Supercritical Fluid Chromatography conditions using a Chiralcel OJ-H 5u, 250 mm L×4.6 mm ID column at 1.2 mL/minutes flow rate using Analytical Supercritical Fluid Chromatography (Berger Instruments, Inc. Newark, Del. USA).

| SFC Instrument: | Berger MultiGram Prep SFC (Berger Instruments, Inc. Newark, DE 19702. |
| --- | --- |
| Column: | Chiralcel OJ-H; 5 u; 250 mm L × 20 mm ID (Chiral Technologies, Inc., Exton, PA, USA) |
| Column temperature: | 35° C. |
| SFC Modifier: | 15% MeOH with 1.0% DEA/85% CO$_2$ |
| Flow rate: | 50 mL/min |
| Outlet Pressure: | 100 bar |
| Detector: | UV at 220 nm |

Step 7: In an analogous manner to EXAMPLE 13, step 2, (1S,2R)-1-(1H-indol-1-yl)-3-(methylamino)-1-(2-methylphenyl)propan-2-ol hydrochloride was prepared as a white solid, from (1S,2R)-1-(1H-indol-1-yl)-3-(methylamino)-1-(2-methylphenyl)propan-2-ol, which was isolated as Peak 1 of the chiral separation (step 6). Chiral purity: 100%. MS (ESI) m/z 295.3 ([M+H]$^+$); HRMS: calcd for $C_{19}H_{22}N_2O$+H$^+$, 295.1805; found (ESI, [M+H]$^+$), 295.1795.

Example 8

(1S,2R)-1-(6-chloro-2,3-dihydro-4H-1,4-benzoxazin-4-yl)-1-(3,5-difluorophenyl)-3-(methylamino) propan-2-ol hydrochloride

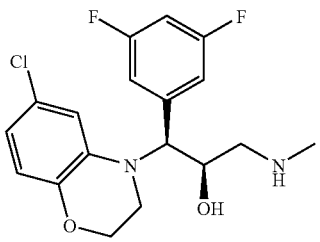

Step 1: In an analogous manner to EXAMPLE 16, step 1,6-chloro-3,4-dihydro-2H-1,4-benzoxazine was prepared from 6-chloro-2H-1,4-benzoxazin-3(4H)-one as a yellow solid. MS (ES) m/z 170.0 ([M+H]$^+$); HRMS: calcd for $C_8H_8ClNO$+H$^+$, 170.0367; found (ESI, [M+H]$^+$), 170.0365.

Step 2: In an analogous manner to EXAMPLE 6, step 4, (2S,3S)-3-(6-chloro-2,3-dihydro-4H-1,4-benzoxazin-4-yl)-3-(3,5-difluorophenyl)propane-1,2-diol was prepared from 6-chloro-3,4-dihydro-2H-1,4-benzoxazine and [(2R,3R)-3-(3,5-difluorophenyl)oxiran-2-yl]methanol (EXAMPLE 157, step 3) as a viscous, yellowish liquid. MS (ES) m/z 356.1 ([M+H]$^+$); HRMS: calcd for $C_{17}H_{16}ClF_2NO_3$+H$^+$, 356.0860; found (ESI, [M+H]$^+$), 356.0869.

Step 3: In an analogous manner to EXAMPLE 6, step 6, (1S,2R)-1-(6-chloro-2,3-dihydro-4H-1,4-benzoxazin-4-yl)-1-(3,5-difluorophenyl)-3-(methylamino)propan-2-ol hydrochloride was prepared from (2S,3S)-3-(6-chloro-2,3-dihydro-4H-1,4-benzoxazin-4-yl)-3-(3,5-difluorophenyl) propane-1,2-diol as a white powder. MS (ES) m/z 369.1 ([M+H]$^+$); HRMS: calcd for $C_{18}H_{19}ClF_2N_2O_2$+H$^+$, 369.1176; found (ESI, [M+H]$^+$), 369.1178.

Example 9

(1S,2R)-1-(3-fluorophenyl)-3-(methylamino)-1-(2-methyl-2,3-dihydro-4H-1,4-benzoxazin-4-yl)propan-2-ol hydrochloride

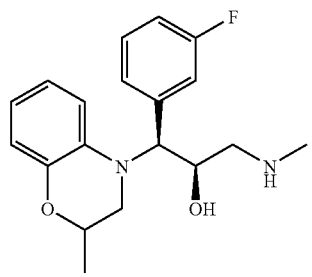

In an analogous manner to EXAMPLE 16, step 1,2-methyl-3,4-dihydro-2H-1,4-benzoxazine was prepared from 2-methyl-2H-1,4-benzoxazin-3(4H)-one[3] as a brown oil. MS (ES) m/z 149.9 ([M+H]$^+$).

[3] Wheeler, K. W. *J. Med. Pharm. Chem.* 1962, 5, 1378-1383.

In an analogous manner to EXAMPLE 6, step 4, (2S,3S)-3-(3-fluorophenyl)-3-(2-methyl-2,3-dihydro-4H-1,4-benzoxazin-4-yl)propane-1,2-diol was prepared from 2-methyl-3,4-dihydro-2H-1,4-benzoxazine and [(2R,3R)-3-(3-fluorophenyl)oxiran-2-yl]methanol (EXAMPLE 6, step 3) as a viscous, brown liquid. MS (ES) m/z 318.2 ([M+H]$^+$); HRMS: calcd for $C_{18}H_{20}FNO_3$+H$^+$, 318.1500; found (ESI, [M+H]$^+$), 318.1513.

In an analogous manner to EXAMPLE 6, step 6, (1S,2R)-1-(3-fluorophenyl)-3-(methylamino)-1-(2-methyl-2,3-dihydro-4H-1,4-benzoxazin-4-yl)propan-2-ol hydrochloride was prepared from (2S,3S)-3-(3-fluorophenyl)-3-(2-methyl-2,3-dihydro-4H-1,4-benzoxazin-4-yl)propane-1,2-diol as a white powder. MS (ES) m/z 331.0 ([M+H]$^+$); HRMS: calcd for $C_{19}H_{23}FN_2O_2$+H$^+$, 331.1816; found (ESI, [M+H]$^+$), 331.1804.

Example 10

(1S,2R)-1-(5-fluoro-3-methyl-1H-indol-1-yl)-3-(methylamino)-1-phenylpropan-2-ol hydrochloride

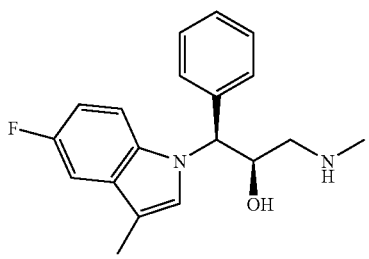

Step 1: To a mixture of 4-fluoro-phenylamine (9 g, 81 mmol), concentrated hydrochloric acid (20.4 mL), and water (35.1 mL) was added sodium nitrite (6.3 g, 89.1 mmol) dissolved in water (7.8 mL). In a separate flask ethyl 2-ethylacetoacetate (14.4 g, 89.1 mmol) in ethanol (63.6 mL) at 0° C. was treated with potassium hydroxide (5.1 g, 89.1 mmol) in water (7.5 mL) and ice and the above solution added. The pH of the reaction was adjusted to 5-6 and the reaction stirred at 0° C. for 3 hours and then stored in the freezer overnight. The reaction was then extracted with ethyl acetate (100 mL) and the organics washed with saturated brine solution (100 mL), dried with anhydrous magnesium sulfate. Most of the solvent was removed in vacuo before it was added dropwise to a 14.5% ethanolic solution of hydrochloric acid (70 mL) at 78° C. Heating was continued for 2 hours. The solvent was removed in vacuo and the residue treated with dichloromethane (300 mL) and water (100 mL). The organic layer was washed with saturated sodium chloride (200 mL), dried over sodium sulfate and concentrated in vacuo. Purification on a short wash column (silica gel, 25% ethyl acetate/hexane) gave ethyl 5-fluoro-3-methyl-1H-indole-2-carboxylate as a white solid. MS (ES) m/z 220.0

Step 2: Ethyl 5-fluoro-3-methyl-1H-indole-2-carboxylate (8.3 g, 37.5 mmol) and potassium hydroxide (6.3 g, 112.5 mmol) in a mixture of ethanol (20 mL) and water (15 mL) was heated at reflux for 1 hour. The volume was reduced to 10 mL under reduced pressure and the solution brought to an acidic pH with a 3N aqueous solution of hydrochloric acid. The resulting precipitate was filtered, washed with water (100 mL) and dried in vacuo at 80° C. overnight to afford 5-fluoro-3-methyl-1H-indole-2-carboxylic acid as a white solid. MS (ES) m/z 192.0

Step 3: 5-fluoro-3-methyl-1H-indole-2-carboxylic acid (8.49 g, 43.9 mmol) and copper metal (0.35 g, 5.5 mmol) in distilled quinoline (22 mL) was heated to reflux for 3 hours. The copper powder was filtered off and the filtrate was brought to pH 3 at 0° C. with a 6N aqueous solution of hydrochloric acid. The solution was extracted with ether (200 mL) and the organics washed with saturated sodium chloride (200 mL), dried over magnesium sulfate and concentrated in vacuo to give 5-fluoro-3-methyl-1H-indole as a brown solid. MS (ES) m/z 150.0.

Step 4: To a solution of diisopropyl D-tartrate (6 mL, 28 mmol) in methylene chloride (800 mL) at −10° C. under nitrogen was added 4A molecular sieves (15 g), titanium isopropoxide (5.9 mL, 20 mmol), and cinnamyl alcohol (27 g, 200 mmol). The mixture was allowed to age for 40 minutes at −10° C., after which time it was cooled to −20° C., and treated in a dropwise fashion with a solution of tert-butyl hydroperoxide (TBHP, ~450 mmol) in isooctane. After 18 hours at −30 to −15° C., the reaction mixture was treated with a 30% aqueous solution of sodium hydroxide (5 mL) and diethyl ether (100 mL). The cold bath was removed and the mixture was allowed to warm to ~10° C. Magnesium sulfate (anhydrous, 15 g) was added and the mixture was stirred for 20 minutes. After the solids settled, the solution was filtered through a pad of silica gel, and washed with ether (50 mL). The filtrate was concentrated in vacuo and toluene was added to azeotropically remove the unreacted TBHP. The residue was then purified using a silica gel column (hexane:ethyl acetate/3:1) and the purified product was crystallized from hexane/ethyl acetate to yield [(2R,3R)-3-phenyloxiran-2-yl] methanol as white crystal (18 g, 60%, 98.2% ee). MS (ESI) m/z 151.

Step 5: A mixture of 5-fluoro-3-methyl-1H-indole (2.91 g, 19.5 mmol) and potassium hydride 50% dispersion in mineral oil (2.8 g, 35.1 mmol) in dichloromethane (40 mL) was stirred for 10 minutes under nitrogen at room temperature. A solution of [(2R,3R)-3-phenyloxiran-2-yl]methanol (2.0 g, 13.0 mmol) and titanium isopropoxide (4.3 mL, 14.3 mmol) in dichloromethane (10 mL) was then added and the mixture was stirred at room temperature for 12 hours. After disappearance of the epoxide, the mixture was partitioned between a 1N aqueous solution of hydrochloric acid (50 mL) and ethyl acetate (50 mL). The organic layer was separated, washed with saturated sodium bicarbonate (50 mL), dried over anhydrous sodium sulfate, filtered, and concentrated in vacuo. The crude product was purified via Biotage chromatography (FlasH40i, silica, 60% ethyl acetate/hexane) to give (2S,3S)-3-(5-fluoro-3-methyl-1H-indol-1-yl)-3-phenylpropane-1,2-diol. MS (ESI) m/z 300

Step 6: A solution of (2S,3S)-3-(5-fluoro-3-methyl-1H-indol-1-yl)-3-phenylpropane-1,2-diol (1.03 g, 3.4 mmol) and p-toluenesulfonyl chloride (0.78 g, 4.1 mmol) in anhydrous pyridine (11 ml) was stirred at room temperature under nitrogen for 12 hours. The reaction was poured into a 1N aqueous solution of hydrochloric acid (50 mL) and extracted with ethyl acetate (50 mL). The organics were dried over anhydrous sodium sulfate, filtered, and concentrated to give (2S,3S)-toluene-4-sulfonic acid 3-(5-fluoro-3-methyl-indol-1-yl)-2-hydroxy-3-phenyl-propyl ester. The product was used in the next step without further purification. To a solution of toluene-4-sulfonic acid 3-(5-fluoro-3-methyl-indol-1-yl)-2-hydroxy-3-phenyl-propyl ester (1.6 g, 3.4 mmol) in methanol (10 mL) was added a 2N solution of methylamine in methanol (8.6 mL, 17 mmol) and the reaction stirred for 12 hours. Upon completion, the reaction was partitioned between saturated sodium bicarbonate (50 mL) and ethyl acetate (50 mL). The organic layer was separated, dried over anhydrous sodium sulfate, filtered, and concentrated in vacuo. The crude product was purified via Biotage chromatography (FlasH40i, silica, 20% MeOH/dichloromethane) to give (1S,2R)-1-(5-fluoro-3-methyl-1H-indol-1-yl)-3-(methylamino)-1-phenylpropan-2-ol as a clear oil. The free base was dissolved in a minimum amount of ethanol and treated with a 2N ethereal solution of hydrochloric acid and stirred for 1 hour. The ethanol was removed in vacuo and the clear oil was triturated with ether/dichloromethane to give (1S,2R)-1-(5-fluoro-3-methyl-1H-indol-1-yl)-3-(methylamino)-1-phenylpropan-2-ol hydrochloride as a white solid. MS (ESI) m/z 313

Example 11

(1RS,2SR)-1-(6-chloro-2,3-dihydro-4H-1,4-benzoxazin-4-yl)-3-(methylamino)-1-phenylpropan-2-ol hydrochloride

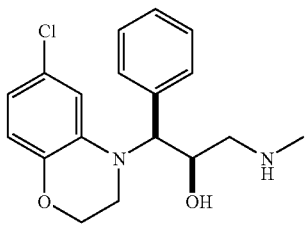

In an analogous manner to EXAMPLE 3, step 1, ethyl (2RS,3RS)-3-(6-chloro-2,3-dihydro-4H-1,4-benzoxazin-4-yl)-2-hydroxy-3-phenylpropanoate was prepared from 6-chloro-3,4-dihydro-2H-1,4-benzoxazine (EXAMPLE 8, step 1) and trans-ethyl-3-phenylglycidate as a viscous, yellow liquid. MS (ESI) m/z 362.0 ([M+H]$^+$); HRMS: calcd for $C_{19}H_{20}ClNO_4{}^+H^+$, 362.1154; found (ESI, [M+H]$^+$), 362.1150.

In an analogous manner to EXAMPLE 3, step 2, (2RS,3RS)-3-(6-chloro-2,3-dihydro-4H-1,4-benzoxazin-4-yl)-2-hydroxy-N-methyl-3-phenylpropanamide was prepared from ethyl (2RS,3RS)-3-(6-chloro-2,3-dihydro-4H-1,4-benzoxazin-4-yl)-2-hydroxy-3-phenyl propanoate as white needles. MS (ESI) m/z 344.9 ([M–H]$^-$);

HRMS: calcd for $C_{18}H_{19}ClN_2O_3+H^+$, 347.1157; found (ESI, [M+H]$^+$), 347.1150.

In an analogous manner to EXAMPLE 3, step 3, (1RS,2SR)-1-(6-chloro-2,3-dihydro-4H-1,4-benzoxazin-4-yl)-3-(methylamino)-1-phenylpropan-2-ol hydrochloride was prepared from (2RS,3RS)-3-(6-chloro-2,3-dihydro-4H-1,4-benzoxazin-4-yl)-2-hydroxy-N-methyl-3-phenylpropanamide as a white powder. MS (ESI) m/z 333.1 ([M+H]$^+$); HRMS: calcd for $C_{18}H_{21}ClN_2O_2+H^+$, 333.1370; found (ESI, [M+H]$^+$), 333.1381.

Example 12

(1RS,2SR)-3-(methylamino)-1-(6-methyl-2,3-dihydro-4H-1,4-benzoxazin-4-yl)-1-phenylpropan-2-ol hydrochloride

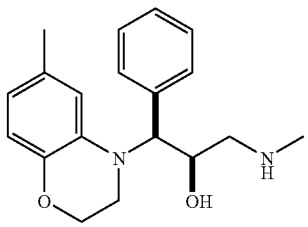

In an analogous manner to EXAMPLE 16, step 1,6-methyl-3,4-dihydro-2H-1,4-benzoxazine was prepared from 6-methyl-2H-1,4-benzoxazine-3(4H)-one as a yellow oil. MS (ES) m/z 150.0 ([M+H]$^+$); HRMS: calcd for $C_9H_{11}NO+H^+$, 150.0919; found (ESI, [M+H]$^+$), 150.0924.

In an analogous manner to EXAMPLE 3, step 1, ethyl (2RS,3RS)-2-hydroxy-3-(6-methyl-2,3-dihydro-4H-1,4-benzoxazin-4-yl)-3-phenylpropanoate was prepared from 6-methyl-3,4-dihydro-2H-1,4-benzoxazine and trans-ethyl-3-phenylglycidate as a viscous, yellow liquid. MS (ESI) m/z 342.0 ([M+H]$^+$); HRMS: calcd for $C_{20}H_{23}NO_4{}^+H^+$, 342.1700; found (ESI, [M+H]$^+$), 342.1683.

In an analogous manner to EXAMPLE 3, step 2, (2RS,3RS)-2-hydroxy-N-methyl-3-(6-methyl-2,3-dihydro-4H-1,4-benzoxazin-4-yl)-3-phenylpropanamide was prepared from ethyl (2RS,3RS)-2-hydroxy-3-(6-methyl-2,3-dihydro-4H-1,4-benzoxazin-4-yl)-3-phenyl propanoate as a white powder. MS (ESI) m/z 325.0 ([M–H]$^-$); HRMS: calcd for $C_{19}H_{22}N_2O_3+H^+$, 327.1703; found (ESI, [M+H]$^+$), 327.1703.

In an analogous manner to EXAMPLE 3, step 3, (1RS,2SR)-3-(methylamino)-1-(6-methyl-2,3-dihydro-4H-1,4-benzoxazin-4-yl)-1-phenylpropan-2-ol hydrochloride was prepared from (2RS,3RS)-2-hydroxy-N-methyl-3-(6-methyl-2,3-dihydro-4H-1,4-benzoxazin-4-yl)-3-phenylpropanamide as a white powder. MS (ESI) m/z 313.0 ([M+H]$^+$); HRMS: calcd for $C_{19}H_{24}N_2O_2+H^+$, 313.1911; found (ESI, [M+H]$^+$), 313.1908.

Example 13

(1S,2R)-1-(6-chloro-2,3-dihydro-4H-1,4-benzoxazin-4-yl)-3-(methylamino)-1-phenylpropan-2-ol hydrochloride

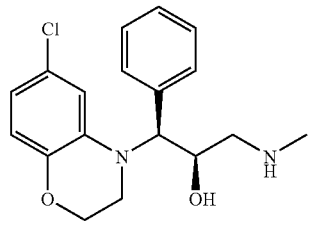

Step 1: Racemic (1RS,2SR)-1-(6-chloro-2,3-dihydro-4H-1,4-benzoxazin-4-yl)-3-(methylamino)-1-phenylpropan-2-ol (EXAMPLE 11) was dissolved in methanol. The resulting solution was injected onto the Supercritical Fluid Chromatography instrument. The baseline resolved enantiomers, using the conditions described below, were collected. The enantiomeric purity of each enantiomer was determined under the same Supercritical Fluid Chromatography conditions using a Chiralpak AD-H 5u, 250 mm×4.6 mm ID column at 2.0 mL/minutes flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 40% MeOH with 0.5% DEA |
| Flow rate: | 50 mL/min |
| Outlet Pressure: | 100 bar |
| Detector: | UV at 266 nm |

Step 2: A solution of (1S,2R)-1-(6-chloro-2,3-dihydro-4H-1,4-benzoxazin-4-yl)-3-(methylamino)-1-phenylpropan-2-ol, isolated as Peak 1, (58 mg, 0.17 mmol) in dichloromethane (3 mL) was treated with an ethereal solution of hydrochloric acid (1 M, 0.2 mL, 0.2 mmol). To the resulting solution was added hexane until white powder formed, which was collected, washed with hexane, and dried in vacuo to yield 62 mg (45%) of (1S,2R)-1-(6-chloro-2,3-dihydro-4H-1,4-benzoxazin-4-yl)-3-(methylamino)-1-phenylpropan-2-ol hydrochloride. Chiral purity: >99.9%. MS (ESI) m/z 333.0 ([M+H]$^+$); HRMS: calcd for $C_{18}H_{21}ClN_2O_2+H^+$, 333.1370; found (ESI, [M+H]$^+$), 333.1372.

Example 14

(1R,2S)-1-(6-chloro-2,3-dihydro-4H-1,4-benzoxazin-4-yl)-3-(methylamino)-1-phenylpropan-2-ol hydrochloride

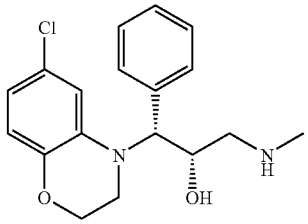

In an analogous manner to EXAMPLE 13, step 2, (1R,2S)-1-(6-chloro-2,3-dihydro-4H-1,4-benzoxazin-4-yl)-3-(methylamino)-1-phenylpropan-2-ol hydrochloride was prepared from (1R,2S)-1-(6-chloro-2,3-dihydro-4H-1,4-benzoxazin-4-yl)-3-(methylamino)-1-phenylpropan-2-ol which was isolated as Peak 2 of the chiral separation (EXAMPLE 13, step 1). Chiral purity: >99.9%. MS (ESI) m/z 333.0 ([M+H]$^+$); HRMS: calcd for $C_{18}H_{21}ClN_2O_2+H^+$, 333.1370; found (ESI, [M+H]$^+$), 333.1374.

Example 15

(1S,2R)-1-(6-chloro-2,3-dihydro-4H-1,4-benzoxazin-4-yl)-1-(3-fluorophenyl)-3-(methylamino)propan-2-ol hydrochloride

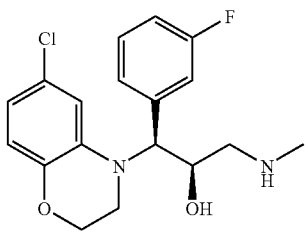

In an analogous manner to EXAMPLE 6, step 4, (2S,3S)-3-(6-chloro-2,3-dihydro-4H-1,4-benzoxazin-4-yl)-3-(3-fluorophenyl)propane-1,2-diol was prepared from 6-chloro-3,4-dihydro-2H-1,4-benzoxazine (EXAMPLE 8, step 1) and [(2R,3R)-3-(3-fluorophenyl)oxiran-2-yl]methanol (EXAMPLE 6, step 3) as a viscous, yellowish liquid. MS (ES) m/z 335.8 ([M–H]$^-$); HRMS: calcd for $C_{20}H_{22}FNO_2+H^+$, 338.0959; found (ESI, [M+H]$^+$), 338.0959.

In an analogous manner to EXAMPLE 6, step 6, (1S,2R)-1-(6-chloro-2,3-dihydro-4H-1,4-benzoxazin-4-yl)-1-(3-fluorophenyl)-3-(methylamino)propan-2-ol hydrochloride was prepared from (2S,3S)-3-(6-chloro-2,3-dihydro-4H-1,4-benzoxazin-4-yl)-3-(3-fluorophenyl)propane-1,2-diol as a white powder. MS (ES) m/z 351.0 ([M+H]$^+$); HRMS: calcd for $C_{18}H_{20}ClFN_2O_2+H^+$, 351.1276; found (ESI, [M+H]$^+$), 351.1276.

Example 16

(1S,2R)-1-(2,2-dimethyl-2,3-dihydro-4H-1,4-benzoxazin-4-yl)-1-(3-fluorophenyl)-3-(methylamino)propan-2-ol hydrochloride

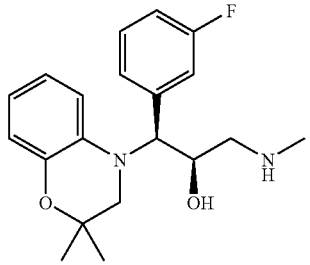

Step 1: To a solution of 2,2-dimethyl-2H-1,4-benzoxazin-3(4H)-one[4] (2.658 g, 15.0 mmol) in tetrahydrofuran (10 mL) under nitrogen was added slowly a solution of borane (1.0 M in tetrahydrofuran, 22.5 mL, 22.5 mmol) via a syringe. The resulting mixture was stirred at room temperature for 10 minutes and then at 70° C. for 1 hour. After cooling, the reaction mixture was quenched with methanol (3 mL) slowly. All volatiles were removed under reduced pressure. A 1 N aqueous solution of hydrochloric acid (10 mL) was added to the liquid residue and the mixture was warmed to 50° C. for 10 minutes. After cooling, the reaction mixture was made alkaline using saturated sodium bicarbonate solution (15 mL), and extracted with ethyl acetate (25 mL). The organic layer was washed with water, brine, dried (anhydrous sodium sulfate), filtered through a pad of silica gel, and concentrated under reduced pressure to yield 2.310 g (94%) of 2,2-dimethyl-3,4-dihydro-2H-1,4-benzoxazine as a brown oil. MS (ES) m/z 164.0 ([M+H]$^+$).

[4] Caliendo, G.; Perissutti, E.; Santagada, V.; Fiorino, F.; Severino, B.; Bianca, R.

Step 2: In an analogous manner to EXAMPLE 6, step 4, (2S,3S)-3-(2,2-dimethyl-2,3-dihydro-4H-1,4-benzoxazin-4-yl)-3-(3-fluorophenyl)propane-1,2-diol was prepared from 2,2-dimethyl-3,4-dihydro-2H-1,4-benzoxazine and [(2R,3R)-3-(3-fluorophenyl)oxiran-2-yl]methanol (EXAMPLE 6, step 3) as a white solid. MS (ES) m/z 332.2 ([M+H]$^+$); HRMS: calcd for $C_{19}H_{22}FNO_3+H^+$, 332.1657; found (ESI, [M+H]$^+$), 332.1648.

Step 3: In an analogous manner to EXAMPLE 6, step 6, (1S,2R)-1-(2,2-dimethyl-2,3-dihydro-4H-1,4-benzoxazin-4-yl)-1-(3-fluorophenyl)-3-(methylamino)propan-2-ol hydrochloride was prepared from (2S,3S)-3-(2,2-dimethyl-2,3-dihydro-4H-1,4-benzoxazin-4-yl)-3-(3-fluorophenyl)propane-1,2-diol as a white powder. MS (ES) m/z 345.2 ([M+H]$^+$); HRMS: calcd for $C_{20}H_{25}FN_2O_2+H^+$, 345.1978; found (ESI, [M+H]$^+$), 345.1981.

Example 17

(1S,2R)-1-(2,2-dimethyl-2,3-dihydro-4H-1,4-benzoxazin-4-yl)-3-(methylamino)-1-phenylpropan-2-ol hydrochloride

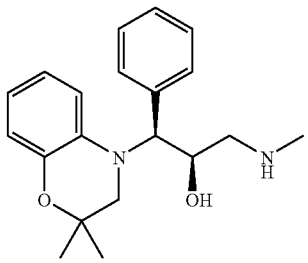

In an analogous manner to EXAMPLE 6, step 4, (2S,3S)-3-(2,2-dimethyl-2,3-dihydro-4H-1,4-benzoxazin-4-yl)-3-phenylpropane-1,2-diol was prepared from 2,2-dimethyl-3,4-dihydro-2H-1,4-benzoxazine (EXAMPLE 16, step 1) and [(2R,3R)-3-phenyloxiran-2-yl]methanol (EXAMPLE 10, step 4) as a white solid. MS (ES) m/z 314.1 ([M+H]$^+$).

In an analogous manner to EXAMPLE 6, step 6, (1S,2R)-1-(2,2-dimethyl-2,3-dihydro-4H-1,4-benzoxazin-4-yl)-3-(methylamino)-1-phenylpropan-2-ol hydrochloride was prepared from (2S,3S)-3-(2,2-dimethyl-2,3-dihydro-4H-1,4-benzoxazin-4-yl)-3-phenylpropane-1,2-diol as a white powder. MS (ES) m/z 327.2 ([M+H]$^+$); HRMS: calcd for $C_{20}H_{26}N_2O_2+H^+$, 327.2073; found (ESI, [M+H]$^+$), 327.2082.

Example 18

(1S,2R)-1-(2,3-dihydro-4H-1,4-benzothiazin-4-yl)-1-(3-fluorophenyl)-3-(methylamino)propan-2-ol hydrochloride

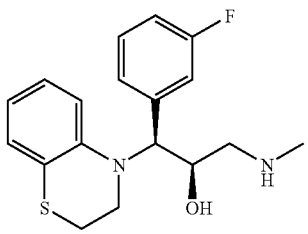

In an analogous manner to EXAMPLE 6, step 4, (2S,3S)-3-(2,3-dihydro-4H-1,4-benzothiazin-4-yl)-3-(3-fluorophenyl)propane-1,2-diol was prepared from 3,4-dihydro-2H-1,4-benzothiazine[5] and [(2R,3R)-3-(3-fluorophenyl)oxiran-2-yl]methanol (EXAMPLE 6, step 3) as a viscous, yellowish liquid. MS (ES) m/z 320.1 ([M+H]$^+$); HRMS: calcd for $C_{17}H_{18}FNO_2S+H^+$, 320.1115; found (ESI, [M+H]$^+$), 320.1113.

[5]El-Subbagh, H. I.; Abadi, A. H.; Al-Khawad, I. E.; Al-Rashood, K. A.; *Arch. Pharm.* 1999, 332, 19-24.

In an analogous manner to EXAMPLE 6, step 6, (1S,2R)-1-(2,3-dihydro-4H-1,4-benzothiazin-4-yl)-1-(3-fluorophenyl)-3-(methylamino)propan-2-ol hydrochloride was prepared from (2S,3S)-3-(2,3-dihydro-4H-1,4-benzothiazin-4-yl)-3-(3-fluorophenyl)propane-1,2-diol as a white powder. MS (ES) m/z 333.1 ([M+H]$^+$); HRMS: calcd for $C_{18}H_{21}FN_2OS+H^+$, 333.1431; found (ESI, [M+H]$^+$), 333.1420.

Example 19

(1S,2R)-1-(3-fluorophenyl)-3-(methylamino)-1-(2-phenyl-2,3-dihydro-4H-1,4-benzoxazin-4-yl)propan-2-ol hydrochloride

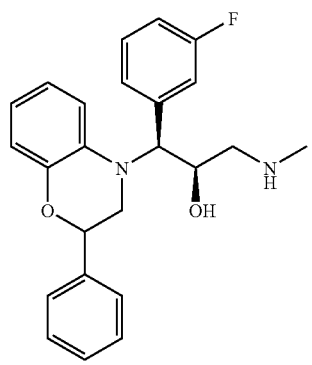

In an analogous manner to EXAMPLE 6, step 4, (2S,3S)-3-(3-fluorophenyl)-3-(2-phenyl-2,3-dihydro-4H-1,4-benzoxazin-4-yl)propane-1,2-diol was prepared from 2-phenyl-3,4-dihydro-2H-1,4-benzoxazine[6] and [(2R,3R)-3-(3-fluorophenyl)oxiran-2-yl]methanol (EXAMPLE 6, step 3) as a white solid. MS (ES) m/z 380.0 ([M+H]$^+$); HRMS: calcd for $C_{23}H_{22}FNO_3+H^+$, 380.1662; found (ESI, [M+H]$^+$), 380.1661.

[6]Olagbemiro, T. O.; Nyakutse, C. A.; Lajide, L.; Agho, M. O.; Chukwu, C. E. *Bull. Soc. Chim. Belg.* 1987, 96, 473-480.

In an analogous manner to EXAMPLE 6, step 6, (1S,2R)-1-(3-fluorophenyl)-3-(methylamino)-1-(2-phenyl-2,3-dihydro-4H-1,4-benzoxazin-4-yl)propan-2-ol hydrochloride was prepared from (2S,3S)-3-(3-fluorophenyl)-3-(2-phenyl-2,3-dihydro-4H-1,4-benzoxazin-4-yl)propane-1,2-diol as a white powder. MS (ES) m/z 393.2 ([M+H]$^+$); HRMS: calcd for $C_{24}H_{25}FN_2O_2+H^+$, 393.1978; found (ESI, [M+H]$^+$), 393.1986.

Example 20

(1S,2R)-1-(3-fluorophenyl)-3-(methylamino)-1-[(2R)-2-phenyl-2,3-dihydro-4H-1,4-benzoxazin-4-yl]propan-2-ol hydrochloride

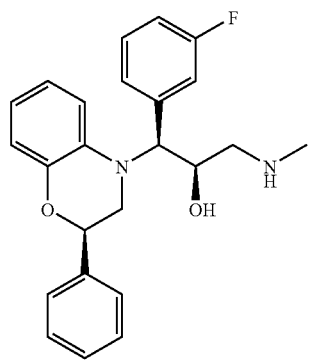

Step 1: Diastereomeric mixture of (1S,2R)-1-(3-fluorophenyl)-3-(methylamino)-1-(2-phenyl-2,3-dihydro-4H-1, 4-benzoxazin-4-yl)propan-2-ol (EXAMPLE 19) was dissolved in methanol. The resulting solution was injected onto the Supercritical Fluid Chromatography instrument. The baseline resolved diastereomers, using the conditions described below, were collected.

| | |
|---|---|
| SFC Instrument: | Berger MultiGram Prep SFC (Berger Instruments, Inc. Newark, DE 19702. |
| Column: | Ethyl pyridine; 250 mm L × 20 mm ID (Princeton Chromatography Inc.) |
| Column temperature: | 35° C. |
| SFC Modifier: | 15% MeOH with 85% $CO_2$ |
| Flow rate: | 50 mL/min |
| Outlet Pressure: | 100 bar |
| Detector: | UV at 220 nm |

Step 2: (1S,2R)-1-(3-fluorophenyl)-3-(methylamino)-1-[(2R)-2-phenyl-2,3-dihydro-4H-1,4-benzoxazin-4-yl]propan-2-ol, isolated as peak 1, was subjected to hydrochloride salt formation in an analogous manner to EXAMPLE 13, step 2 to give (1S,2R)-1-(3-fluorophenyl)-3-(methylamino)-1-[(2R)-2-phenyl-2,3-dihydro-4H-1,4-benzoxazin-4-yl]propan-2-ol hydrochloride as a white powder. MS (ES) m/z 393.2 ([M+H]$^+$); HRMS: calcd for $C_{24}H_{25}FN_2O_2$+H$^+$, 393.1973; found (ESI, [M+H]$^+$), 393.1992.

Example 21

(1S,2R)-1-(3-fluorophenyl)-3-(methylamino)-1-[(2S)-2-phenyl-2,3-dihydro-4H-1,4-benzoxazin-4-yl]propan-2-ol hydrochloride

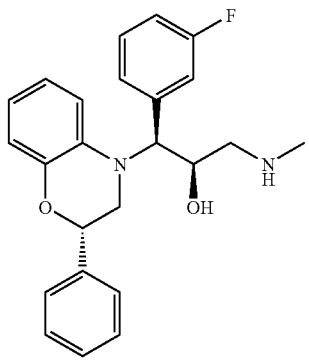

In an analogous manner to EXAMPLE 20, (1S,2R)-1-(3-fluorophenyl)-3-(methylamino)-1-[(2S)-2-phenyl-2,3-dihydro-4H-1,4-benzoxazin-4-yl]propan-2-ol hydrochloride was prepared as a white powder from (1S,2R)-1-(3-fluorophenyl)-3-(methylamino)-1-[(2S)-2-phenyl-2,3-dihydro-4H-1,4-benzoxazin-4-yl]propan-2-ol, which was isolated as peak 2 of the diastereomeric separation (EXAMPLE 20, step 1). MS (ES) m/z 393.2 ([M+H]$^+$); HRMS: calcd for $C_{24}H_{25}FN_2O_2$+H$^+$, 393.1973; found (ESI, [M+H]$^+$), 393.1982.

Cell Lines, Culture Reagents, and Assays

MDCK-Net6 cells, stably transfected with human hNET (Pacholczyk, T., R. D. Blakely, and S. G. Amara, *Nature*, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 □g/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% $CO_2$). On day 2, growth medium was replaced with 200 μl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 μM pargyline. Plates containing cells with 200 μl of assay buffer were equilibrated for 10 minutes at 37° C. prior to addition of compounds. A stock solution of desipramine was prepared in DMSO (10 mM) and delivered to triplicate wells containing cells for a final test concentration of 1 μM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 μl of assay buffer. The cells in assay buffer with test compounds were incubated for 20 minutes at 37° C. To initiate the NE uptake, [$^3$H]NE diluted in assay buffer (120 nM final assay concentration) was delivered in 25 μl aliquots to each well and the plates were incubated for 5 minutes (37° C.). The reaction was terminated by decanting the supernatant from the plate. The plates containing cells were washed twice with 200 μl assay buffer (37° C.) to remove free radioligand. The plates were then inverted, left to dry for 2 minutes, then reinverted and air-dried for an additional 10 minutes. The cells were lysed in 25 μl of 0.25 N NaOH solution (4° C.), placed on a shake table and vigorously shaken for 5 minutes. After cell lysis, 75 μl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report (Prasad, et al., *Placenta*, 1996. 17(4): 201-7). On day 1, cells were plated at 15,000 cells/well in 96-well plates containing growth medium (RPMI 1640 with 10% FBS) and maintained in a cell incubator (37° C., 5% $CO_2$). On day 2, cells were stimulated with staurosporine (40 nM) to increase the expression of the 5-HT transporter [17]. On day 3, cells were removed from the cell incubator two hours prior to assay and maintained at room temperature to equilibrate the growth medium to ambient oxygen concentration. Subsequently, the growth medium was replaced with 200 μl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 μM pargyline. A stock solution of paroxetine (AHR-4389-1) was prepared in DMSO (10 mM) and delivered to triplicate wells containing cells for a final test concentration of 1 μM. Data from these wells were used to define non-specific 5-HT uptake (minimum 5-HT uptake). Test compounds were prepared in DMSO (10 mM)

and diluted in assay buffer according to test range (1 to 1,000 nM). Twenty-five microliters of assay buffer (maximum 5-HT uptake) or test compound were added directly to triplicate wells containing cells in 200 μl of assay buffer. The cells were incubated with the compound for 10 minutes (37° C.). To initiate the reaction, [$^3$H]hydroxytryptamine creatinine sulfate diluted in assay buffer was delivered in 25 μl aliquots to each well for a final test concentration of 15 nM. The cells were incubated with the reaction mixture for 5 minutes at 37° C. The 5-HT uptake reaction was terminated by decanting the assay buffer. The cells were washed twice with 200 μl assay buffer (37° C.) to remove free radioligand. The plates were inverted and left to dry for 2 minutes, then reinverted and air-dried for an additional 10 minutes. Subsequently, the cells were lysed in 25 μl of 0.25 N NaOH (4° C.) then placed on a shaker table and shaken vigorously for 5 minutes. After cell lysis, 75 μl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 μM desipramine (hNET) or 1 μM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment. The results are reported in Table 1.

TABLE 1

| Example | % Inhibition @ 1 μM (hNET) |
|---------|---------------------------|
| 2 | 33.7 |
| 4 | 46.2 |
| 5 | 52.9 |
| 8 | 12.5 |
| 9 | 53.9 |
| 11 | 60.6 |
| 12 | 3.4 |
| 13 | 38.6 |
| 14 | 41.5 |
| 15 | 41.4 |
| 16 | 10 |
| 17 | 9.3 |
| 18 | 90.4 |
| 19 | 95 |
| 20 | 97.2 |
| 21 | 51.7 |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:
1. A compound of formula I:

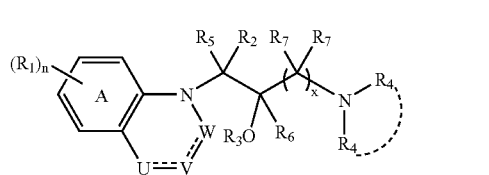

or a pharmaceutically acceptable salt thereof;
wherein:
the dotted line represents an optional double bond between U and V or V and W;
U is, independently, S, SO, or $SO_2$;
W is CH, $CH_2$, or C=O;
V is $C(R_8)$ or $C(R_8)_2$;
$R_1$ is, independently at each occurrence, alkyl, alkoxy, halo, $CF_3$, $OCF_3$, arylalkyloxy substituted with 0-3 $R_9$, aryloxy substituted with 0-3 $R_9$, aryl substituted with 0-3 $R_9$, heteroaryl substituted with 0-3 $R_9$, hydroxy, alkanoyloxy, nitro, nitrile, alkenyl, alkynyl, alkylsulfoxide, phenylsulfoxide substituted with 0-3 $R_9$, alkylsulfone, phenylsulfone substituted with 0-3 $R_9$, alkylsulfonamide, phenylsulfonamide substituted with 0-3 $R_9$, heteroaryloxy substituted with 0-3 $R_9$, heteroarylmethyloxy substituted with 0-3 $R_9$, alkylamido, or phenylamido substituted with 0-3 $R_9$; or two adjacent $R_1$ also represent methylenedioxy;
$R_2$ is aryl substituted with 0-3 $R_1$ or heteroaryl substituted with 0-3 $R_1$;
$R_3$ is H, $C_1$-$C_4$ alkyl substituted with 0-3 $R_1$, $C_3$-$C_6$ cycloalkyl, or phenyl substituted with 0-3 $R_1$;
$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl, or
both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$-$C_4$ alkyl, F, or $CF_3$;
$R_5$ is H or $C_1$-$C_4$ alkyl;
$R_6$ is H or $C_1$-$C_4$ alkyl;
$R_7$ is, independently at each occurrence, H, or $C_1$-$C_4$ alkyl, or
$R_7$ and $R_4$ together with the nitrogen to which $R_4$ is attached form a nitrogen-containing ring containing 3-6 carbon atoms;
$R_8$ is, independently at each occurrence, H, $C_1$-$C_4$ alkyl, $C_3$-$C_6$ heteroalkyl, or aryl substituted with 0-3 $R_1$;
$R_9$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_9$ also represent methylenedioxy;

n is an integer from 0 to 4;

x is an integer from 1 to 2; and wherein 1-3 carbon atoms in ring A may optionally be replaced with N.

2. A compound according to claim 1, wherein: W is $CH_2$.

3. A compound according to claim 1, wherein:
$R_1$ is halo.

4. A compound according to claim 3, wherein:
$R_1$ is fluoro or chloro.

5. A compound according to claim 1, wherein:
$R_2$ is aryl substituted with 0-3 $R_1$.

6. compound according to claim 5, wherein: aryl is phenyl.

7. A compound according to claim 1, wherein:
$R_3$ is H or $C_1$ alkyl.

8. A compound according to claim 1, wherein:
$R_4$ is H or $C_1$-$C_4$ alkyl.

9. A compound according to claim 8, wherein:
$R_4$ is H, methyl, ethyl, or isopropyl.

10. A compound according to claim 1, wherein:
both $R_4$ groups, together with the nitrogen through which they are attached, form a pyridine, piperidine, piperazine, or morpholine ring.

11. A compound according to claim 1, wherein:
$R_5$ is, independently at each occurrence, H or $C_1$ alkyl.

12. A compound according to claim 1, wherein:
n is 0 or 1.

13. A compound according to claim 1, which is
1-(2,3-dihydro-4H-1,4-benzothiazin-4-yl)-1-(3-fluorophenyl)-3-(methylamino)propan-2-ol;
a pharmaceutically acceptable salt thereof.

14. A compound according to claim 1, which is
(1S, 2R)-1-(2,3-dihydro-4H-1,4-benzothiazin-4-yl)-1-(3-fluorophenyl)-3-(methylamino)propan-2-ol;
a pharmaceutically acceptable salt thereof.

15. A composition, comprising:
a. at least one compound according to claim 1; and
b. at least one pharmaceutically acceptable carrier.

* * * * *